United States Patent
Yang et al.

(10) Patent No.: US 10,150,951 B2
(45) Date of Patent: Dec. 11, 2018

(54) PROCESS FOR PRODUCING N-PROPANOL AND PROPIONIC ACID USING METABOLICALLY ENGINEERED PROPIONIBACTERIA

(71) Applicants: Dow Global Technologies LLC, Midland, MI (US); Ohio State University, Columbus, OH (US)

(72) Inventors: Shang-Tian Yang, Dublin, OH (US); Ehab Ammar, Columbus, OH (US); Christopher C. Stowers, Indianapolis, IN (US); Brandon A. Rodriguez, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 457 days.

(21) Appl. No.: 14/653,123

(22) PCT Filed: Dec. 16, 2013

(86) PCT No.: PCT/US2013/075248
§ 371 (c)(1),
(2) Date: Jun. 17, 2015

(87) PCT Pub. No.: WO2014/099707
PCT Pub. Date: Jun. 26, 2014

(65) Prior Publication Data
US 2015/0366248 A1 Dec. 24, 2015

Related U.S. Application Data

(60) Provisional application No. 61/740,490, filed on Dec. 21, 2012.

(51) Int. Cl.
| | | |
|---|---|---|
| *C12N 9/04* | (2006.01) | |
| *C12N 9/02* | (2006.01) | |
| *A23L 19/00* | (2016.01) | |
| *C12P 7/04* | (2006.01) | |
| *C12P 7/52* | (2006.01) | |

(52) U.S. Cl.
CPC ............ *C12N 9/0006* (2013.01); *A23L 19/01* (2016.08); *A23L 19/09* (2016.08); *C12N 9/0008* (2013.01); *C12P 7/04* (2013.01); *C12P 7/52* (2013.01); *C12Y 101/01001* (2013.01); *C12Y 102/01003* (2013.01); *C12Y 102/01* (2013.01)

(58) Field of Classification Search
None
See application file for complete search history.

(56) References Cited

U.S. PATENT DOCUMENTS 5,563,069 A   10/1996 Yang

FOREIGN PATENT DOCUMENTS

| JP | 2011-524749 A | 9/2011 |
|---|---|---|
| WO | 2008/098254 A2 | 8/2008 |
| WO | 2009/154624 A1 | 12/2009 |
| WO | 2011/029166 A1 | 3/2011 |
| WO | 2012/067510 A1 | 5/2012 |

OTHER PUBLICATIONS

Accession P0A9Q7. Jul. 19, 2005.*
Chica et al. Curr Opin Biotechnol. Aug. 2005;16(4):378-84.*
Singh et al. Curr Protein Pept Sci. 2017, 18, 1-11.*
Accession P0A9Q8. Jul. 19, 2005.*
Ariane, Plant Molecular Biology, 2003, vol. 53, No. 1-2, p. 175-188.
Atsumi, Appl. Environ. Microbiol., 2008, vol. 74, p. 7802-7808.
Barbirato, Applied Microbiology Biotechnology, 1997, vol. 47, p. 441-446.
Berríos-Rivera, J. Ind. Microbiol. Biotechnol., 2003, vol. 30, p. 34-40.
Boyaval, Lait., 1995, vol. 75, p. 453-461.
Bruant, PLOS One (www.plosone.org), 2010, vol. 5, Issue 9, p. e13033.
Carta, Bioresource Technology, 1999, vol. 68, p. 23-28.
Chen, Bioprocess. Biosyst. Eng., 2012, vol. 35, p. 469-475.
Coral, Appl. Biochem. Biotechnol., 2008, vol. 151, p. 333-341.
Cousin, PLoS One, 2007, vol. 7, p. e31892.
Da Silva, Biotechnol. Adv., 2009, vol. 27, p. 30-39.
Durfee, J. Bacteriology, 2008, vol. 190, No. 7, p. 2597-2606.
Eden, Appl. Microbiol. Biotechnol., 2001, vol. 55, p. 296-300.
El-Samragy, Int. J. Food Microbiol., 1996. vol. 29, p. 411-416.
Faye, Appl. Environ. Microbiol., 2008, vol. 74, p. 3615-3617.
Feng, Bioresour. Technol., 2011, vol. 102, p. 6141-6146.
Janssen, 2004, Arch. Microbiol., vol. 182, p. 482-486.
Mohamed, Applied Microbiology and Biotechnology, 2013, vol. 97, No. 10, p. 4677-4690.
Murooka, Lait, 2005, vol. 85, No. 1-2, p. 9-22.
Nair, J. Bacteriology, 1994, vol. 176, p. 871-885.
Parizzi, BMC Genomics, 2012, vol. 13, p. 562-602.
Piao, J. Biosci. and Bioeng., 2004, vol. 97, No. 5, p. 310-316.
Suwannakham, Biotechnology and Bioengineering, 2006, vol. 94, p. 383-395.
Suwannakham, Biotechnol. Bioeng., 2005, vol. 91, p. 325-337.
Wang, Bioresouce Technology, 2013, vol. 137, p. 116-123.

(Continued)

Primary Examiner — Christian L Fronda
(74) Attorney, Agent, or Firm — Dinsmore & Shohl LLP

(57) ABSTRACT

A method is provided for making a banana or plantain product comprising providing at least one unpeeled banana or plantain comprising banana or plantain peel and banana or plantain pulp, subjecting the at least one unpeeled banana or plantain to a heat treatment at a temperature and for a time sufficient to gelatinize starch present in the at least one unpeeled banana or plantain to form at least one heat treated unpeeled banana or plantain, and comminuting the at least one heat treated unpeeled banana or plantain to form a banana or plantain puree. A functional food ingredient is also provided comprising a banana or plantain puree including banana or plantain pulp and optionally banana or plantain peel. Foods containing banana or plantain puree or powder are provided, including crackers, snack bars, cereals, smoothies, and cookies.

12 Claims, 23 Drawing Sheets

Specification includes a Sequence Listing.

(56) References Cited

OTHER PUBLICATIONS

Xue, J. Microbiol. Methods, 1999, vol. 34, p. 183-191.
Yang, Process Biochem., 2009, vol. 44, p. 1346-1351.
Yu, Metabolic Engineering, 2011, vol. 12, p. 373-382.
PCT/US2013/075248, Aug. 1, 2014, International Search Report and Written Opinion.
PCT/US2013/075248, Apr. 23, 2015, International Preliminary Report on Patentability.
PCT/US2013/075248, Oct. 21, 2014, Response to the Written Opinion.
Bifunctional acetaldehyde-CoA/alcohol dehydrogenase [*Escherichia coli* str. K-12 substr. DH10B]; GenPept [online] Accession No. YP_001730188.1; Jan. 23, 2012; p. 1-2; URL:https://www.ncbi.nlm.nih.gov/protein/170080868?sat=17&satkey=24215987.
Japanese Office Action dated Oct. 10, 2017 pertaining to Japanese Patent Application No. 2015-549520.
Chinese Office Action pertaining to Chinese Application No. 201380064321.1 dated Jun. 29, 2018.

\* cited by examiner

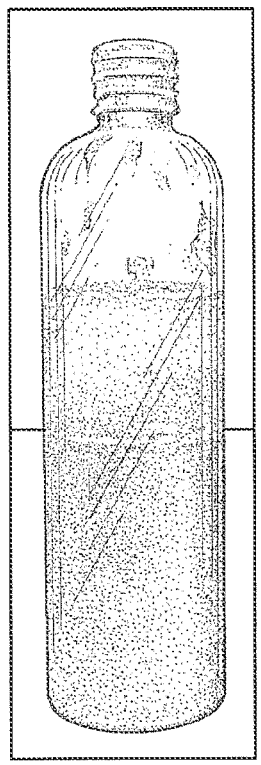 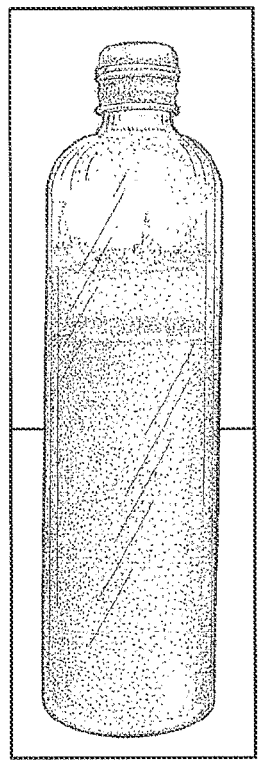 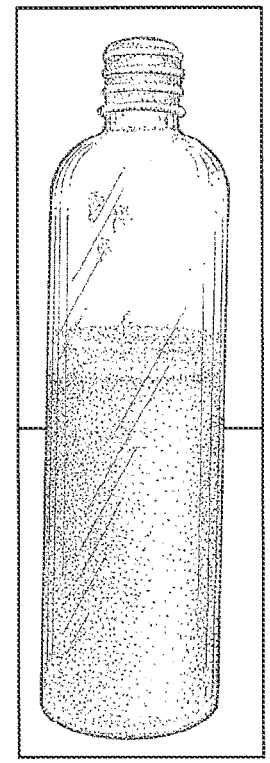
FIG. 15a   FIG. 15b   FIG. 15c
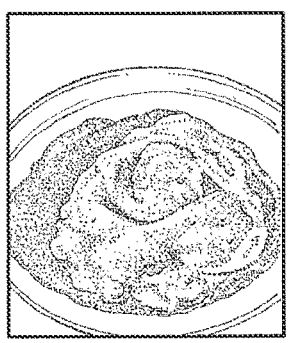 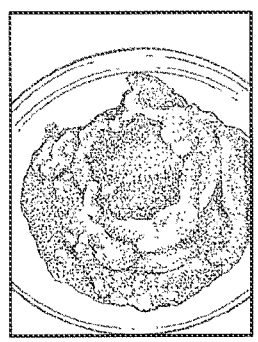 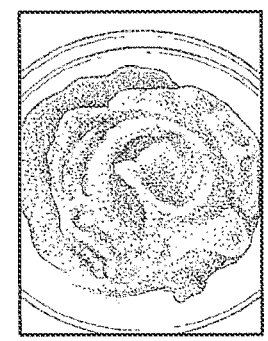
FIG. 16a   FIG. 16b   FIG. 16c

Nutrition Facts

Serving Size (31g)
Servings Per Container

Amount Per Serving

| Calories 30 | Calories from Fat 0 |
|---|---|

| | % Daily Value* |
|---|---|
| Total Fat 0g | 0% |
|    Saturated Fat 0g | 0% |
|    Trans Fat 0g | |
| Cholesterol 0mg | 0% |
| Sodium 130mg | 5% |
| Potassium 230mg | 7% |
| Total Carbohydrate 7g | 2% |
|    Dietary Fiber 1g | 4% |
|    Sugars 4g | |
| Protein 1g | |

| Vitamin A 2% | • | Vitamin C 6% |
|---|---|---|
| Calcium 0% | • | Iron 4% |
| Folate 2% | • | Phosphorus 2% |

*Percent Daily Values are based on a 2,000 calorie diet. Your daily values may be higher or lower depending on your calorie needs.

| | | Calories | 2,000 | 2,500 |
|---|---|---|---|---|
| Total Fat | Less Than | | 65g | 80g |
|   Saturated Fat | Less Than | | 20g | 25g |
| Cholesterol | Less Than | | 300mg | 300 mg |
| Sodium | Less Than | | 2,400mg | 2,400mg |
| Potassium | | | 3,500 mg | 3,500 mg |
| Total Carbohydrate | | | 300g | 375g |
|   Dietary Fiber | | | 25g | 30g |

Calories per gram:
   Fat 9 • Carbohydrate 4 • Protein 4

FIG. 18b

Nutrition Facts

Serving Size (31g)
Servings Per Container

Amount Per Serving

| Calories 25 | Calories from Fat 0 |
|---|---|

| | % Daily Value* |
|---|---|
| Total Fat 0g | 0% |
|    Saturated Fat 0g | 0% |
|    Trans Fat 0g | |
| Cholesterol 0mg | 0% |
| Sodium 0mg | 0% |
| Potassium 80mg | 2% |
| Total Carbohydrate 6g | 2% |
|    Dietary Fiber 0g | 0% |
|    Sugars 2g | |
| Protein 0g | |

| Vitamin A 2% | • | Vitamin C 4% |
|---|---|---|
| Calcium 0% | • | Iron 0% |

*Percent Daily Values are based on a 2,000 calorie diet. Your daily values may be higher or lower depending on your calorie needs:

| | Calories | 2,000 | 2,500 |
|---|---|---|---|
| Total Fat | Less Than | 65g | 80g |
|   Saturated Fat | Less Than | 20g | 25g |
| Cholesterol | Less Than | 300mg | 300 mg |
| Sodium | Less Than | 2,400mg | 2,400mg |
| Potassium | | 3,500 mg | 3,500 mg |
| Total Carbohydrate | | 300g | 375g |
|   Dietary Fiber | | 25g | 30g |

Calories per gram:
   Fat 9 • Carbohydrate 4 • Protein 4

FIG. 19b

PROCESS FOR PRODUCING N-PROPANOL AND PROPIONIC ACID USING METABOLICALLY ENGINEERED PROPIONIBACTERIA

CROSS-REFERENCE TO RELATED APPLICATIONS

This application claims priority to U.S. application Ser. No. 13/728,222 filed on Dec. 27, 2012, which is incorporated herein in its entirety.

FIELD OF THE INVENTION

This invention relates to processing of edible fruits of genus *Musa* (*Musa acuminate* and *Musa balbisiana*) and related species with peels at all maturity levels, and peeled immature fruits of the same species for their use in food or beverage products as functional ingredients.

BACKGROUND

Bananas and plantains, edible fruits of genus *Musa*, comprise large amounts of carbohydrates, particularly starch and sugars. In green bananas, the carbohydrate is present largely in the form of starch, including starch resistant to digestion. As the banana ripens from green to yellow, enzymes within the banana convert the starch into sugars, thereby imparting a sweet flavor to the ripened banana. Green plantains contain an even greater proportion of starch to sugars than green bananas, lending the unripe plantains a neutral flavor. Plantains develop a slightly sweet taste upon becoming ripe (i.e., yellow), with a significant sweet taste when overripe (i.e., black).

Commercial banana puree is processed from ripened yellow bananas after peeling, grinding, pasteurizing and packaging. Some banana purees are dehydrated by employing a suitable dryer, such as a drum dryer, to form banana powder or flakes. Such banana purees, powders or flakes are typically used for food, snack and beverage production as nutritional ingredients in the products. As noted above, unripe, green bananas contain more starch and less reducing sugar than ripe, yellow bananas. The use of green bananas has various benefits for the food, snack and beverage industries due to the presence of large amounts of starch in green bananas; however, due to the technical difficulties involved in the peeling and pureeing processes caused by the harder texture of green bananas as compared to yellow bananas, it has not yet been possible to produce green banana puree at the same cost of yellow banana puree production. Similar to green bananas, both green and yellow plantains have a sufficiently hard texture that they must be cooked prior to any processing, and would also benefit from a low cost production process.

It would be desirable to provide banana puree and plantain puree regardless of the ripeness of the banana or plantain, respectively. It would further be desirable to provide a process for making banana puree and plantain puree employing only natural process steps. Moreover, it would be desirable to incorporate a functional fruit ingredient into food or beverage products to provide both a function and enhanced nutritional value to the products.

SUMMARY

The invention may be embodied in various exemplary and nonlimiting forms. In particular, this Summary is intended merely to illuminate various embodiments of the invention and does not impose a limitation on the scope of the invention.

In accordance with one aspect, a method is provided for making a banana product comprising providing at least one unpeeled banana comprising banana peel and banana pulp, subjecting the at least one unpeeled banana to a heat treatment at a temperature and for a time sufficient to gelatinize starch present in the at least one unpeeled banana to form at least one heat treated unpeeled banana, and comminuting the at least one heat treated unpeeled banana to form a banana puree. The at least one banana is an unripe green banana, a ripe yellow banana, or combinations thereof. In certain embodiments, the temperature comprises at least 70 degrees Celsius and the time comprises at least ten minutes. In certain aspects, the method further comprises drying the banana puree to form a banana powder.

In accordance with another aspect, a method is provided for making a plantain product comprising providing at least one unpeeled plantain comprising plantain peel and plantain pulp, subjecting the at least one unpeeled plantain to a heat treatment at a temperature and for a time sufficient to gelatinize starch present in the at least one unpeeled plantain to form at least one heat treated unpeeled plantain, and comminuting the at least one heat treated unpeeled plantain to form a plantain puree. The at least one plantain is an unripe green plantain, a ripe yellow plantain, an overripe black plantain, or combinations thereof. In certain embodiments, the temperature comprises at least 70 degrees Celsius and the time comprises at least ten minutes. In certain aspects, the method further comprises drying the plantain puree to form a plantain powder.

In another aspect, a method is provided for making a banana product comprising providing at least one unpeeled banana comprising banana peel and banana pulp, subjecting the at least one unpeeled banana to a heat treatment to form at least one heat treated unpeeled banana, peeling the at least one heat treated unpeeled banana, and comminuting the at least one heat treated peeled banana to form a banana puree. In certain embodiments, the temperature comprises at least 70 degrees Celsius and the time comprises at least ten minutes. In certain aspects, the method further comprises drying the banana puree to form a banana powder.

In another aspect, a method is provided for making a plantain product comprising providing at least one unpeeled plantain comprising plantain peel and plantain pulp, subjecting the at least one unpeeled plantain to a heat treatment to form at least one heat treated unpeeled plantain, peeling the at least one heat treated unpeeled plantain, and comminuting the at least one heat treated peeled plantain to form a plantain puree. In certain embodiments, the temperature comprises at least 70 degrees Celsius and the time comprises at least ten minutes. In certain aspects, the method further comprises drying the plantain puree to form a plantain powder.

In another aspect, the invention relates to a functional food ingredient comprising a banana puree that comprises banana pulp and optionally banana peel. According to certain aspects the banana puree is dried and thereby provided in the form of a dried banana powder or flake. The functional food ingredient optionally performs as one or more of the following ingredient types: (1) a natural gluten substitute, (2) a natural gelling agent, (3) a natural fiber fortifying ingredient, (4) a texture modifier, (5) a viscosity enhancer, (6) a dispersing agent, (7) an emulsifying agent, (8) a dip and whip base for food, snack and beverage products, (9) a natural binder, (10) a bulking agent, (11) a sugar substitute, and combinations of any of them.

In another aspect, the invention relates to a functional food ingredient comprising a plantain puree that comprises plantain pulp and optionally plantain peel. According to certain aspects the plantain puree is dried and thereby provided in the form of a dried plantain powder or flake. The functional food ingredient optionally performs as one or more of the following ingredient types: (1) a natural gluten substitute, (2) a natural gelling agent, (3) a natural fiber fortifying ingredient, (4) a texture modifier, (5) a viscosity enhancer, (6) a dispersing agent, (7) an emulsifying agent, (8) a dip and whip base for food, snack and beverage products, (9) a natural binder, (10) a bulking agent, (11) a sugar substitute, and combinations of any of them.

In yet another aspect, the invention relates to a cracker comprising at least one whole grain flour, starch, baking powder, and at least one of green banana powder, green banana puree, green plantain powder, green plantain puree, yellow plantain powder, and yellow plantain puree.

In a further aspect, the invention relates to a snack bar comprising grains, fruit juice, and at least one of green banana powder, green banana puree, green plantain powder, green plantain puree, yellow plantain powder, and yellow plantain puree.

In yet a further aspect, the invention relates to a cereal comprising grains and at least one of green banana powder, green banana puree, green plantain powder, green plantain puree, yellow plantain powder, and yellow plantain puree.

In another aspect, the invention relates to a smoothie comprising fruit selected from the group consisting of fruit juice, dried fruit, fresh fruit, frozen fruit, fruit puree, and combinations thereof, and at least one of green banana powder, green banana puree, green plantain powder, green plantain puree, yellow plantain powder, and yellow plantain puree.

In yet a further aspect, the invention relates to a cookie comprising flour, shortening, at least one sweetener, and at least one of green banana powder, green banana puree, green plantain powder, green plantain puree, yellow plantain powder, and yellow plantain puree.

It will be appreciated by those skilled in the art, given the benefit of the following description of certain exemplary embodiments of the methods and products disclosed here, that at least certain embodiments of the invention have improved or alternative formulations suitable to provide desirable taste profiles, nutritional characteristics, etc. These and other aspects, features and advantages of the invention or of certain embodiments of the invention will be further understood by those skilled in the art from the following description of exemplary embodiments.

BRIEF DESCRIPTION OF THE DRAWINGS

FIG. 15a shows a control beverage composition including fruit puree, oat flour and fruit solids.

FIG. 15b shows a beverage composition including fruit puree, oat flour, fruit solids, and heat treated green banana pulp puree.

FIG. 15c shows a beverage composition including fruit puree, oat flour, fruit solids, and heat treated whole green banana puree.

FIG. 16a shows a berry dip containing heat treated whole green banana powder.

FIG. 16b shows a marinara pizza dip containing heat treated whole green banana powder.

FIG. 16c shows a pineapple banana dip containing heat treated whole green banana powder.

FIG. 18b shows Nutrition Facts for the dip of FIG. 18a.

FIG. 19b shows Nutrition Facts for the dip of FIG. 19a.

DETAILED DESCRIPTION OF EMBODIMENTS

Figure 1A:
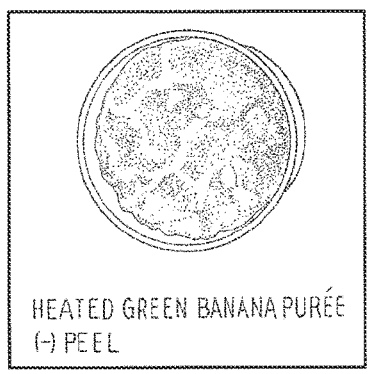
FIG. 1a shows heat treated green banana puree pulp (without peel).

As noted above, green bananas and green and yellow plantains are difficult to process due to the hard texture of both the peel and the pulp. It is an advantage of at least certain embodiments of the invention to provide methods for preparing banana puree, dried banana powder, plantain puree, and dried plantain powder. It is another advantage of the invention to provide economical banana puree, banana powder, plantain puree, and plantain powder. It is an advantage of at least certain embodiments of the invention to provide natural functional ingredients comprising banana puree or plantain puree. It is an advantage of at least certain embodiments of the invention to provide banana puree or banana powder comprising banana peel and banana pulp. It is an advantage of at least certain embodiments of the invention to provide plantain puree or plantain powder comprising plantain peel and plantain pulp. It is an advantage of at least certain embodiments of the invention to provide food and beverage products having desirable appearance, taste and health properties.

As used herein, the terms "green banana" and "unripe banana" are synonymous and used interchangeably. As used herein, the terms "green banana" and "unripe banana" refer to a banana having a color rating of 3 or less on the following color scale of 1 through 7: a banana having a peel that is all green has a color rating of 1, a banana having a peel that is green with a trace of yellow has a color rating of 2, a banana having a peel that is more green than yellow has a color rating of 3, a banana having a peel that is more yellow than green has a color rating of 4, a banana having a peel that is yellow with a trace of green has a color rating of 5, a banana having a peel that is all yellow has a color rating of 6, and a banana having a peel that is all yellow with brown speckles has a color rating of 7. In contrast to unripe or green bananas, as used herein, the terms "yellow banana" and "ripe banana" refer to a banana having a color rating of 4 or more on the color scale of 1 through 7.

The same color scale applies to plantains, and the synonymous and interchangeable terms "green plantain" and "unripe plantain" refer to a plantain having a color rating of 3 or less on the color scale of 1 through 7. The synonymous and interchangeable terms "yellow plantain" and "ripe plantain" refer to a plantain having a color rating of 4 or more on the color scale of 1 through 7. The term "overripe plantain" refers to a plantain that has a peel with more brown or black color than yellow color.

Green bananas, green plantains, and yellow plantains are too firm to be fed into standard commercial automatic banana peelers, thus must be peeled by other methods, such as by hand. Moreover, even after peeling, the hard banana or plantain pulp (i.e., flesh) is difficult and slow to grind, requiring high feeding pump pressures in the commercial pureeing lines. As used herein, the term "pulp" refers to the fruit flesh of a banana or of a plantain. As a result, green bananas are time-consuming and thus expensive to process into green banana puree. Likewise, green and yellow plantains are time-consuming to process into puree.

The firmness of whole green bananas, whole green plantains, and whole yellow plantains may be softened using thermal processes to allow for greater ease of processing, such as peeling, pureeing, and pumping. By softening the peel and pulp of a green banana, for instance, the whole green banana may then be processed on a commercial line without incurring any additional costs. More specifically, the softened peel is easily removed using an automatic banana peeler and the softened pulp is capable of being pureed using the same pureeing and pasteurizing process conditions as yellow bananas. Alternatively, instead of removing the peel from a heat treated bananas, whole unpeeled bananas are also suitable for pureeing to form whole banana puree, powder or flake with peels regardless of its ripening stage to modify the physical and chemical functionalities of food or beverage products. The same principles apply to green and yellow plantains as green bananas.

Typically, to produce yellow banana puree, processing is performed following the intentional harvest of yellow ripened banana at the farm level, or after post-harvest ripening of the green banana to yellow. The pureeing of green bananas can therefore provide benefits to the farmers and initial processors because there is no requirement for differentiating the banana harvest or storage for the fresh fruit purpose or pureeing process purpose with respect to the ripening stage. Farmers can harvest only green bananas, green plantains, and yellow plantains, and processors can puree the whole green banana, green plantain, yellow plantain, or yellow banana using this invention through the simplified raw material collection and handling.

In certain embodiments of the invention, a method is provided for making a banana product comprising providing at least one unpeeled banana comprising banana peel and banana pulp, subjecting the at least one unpeeled banana to a heat treatment at a temperature and for a time sufficient to gelatinize starch present in the at least one unpeeled banana to form at least one heat treated unpeeled banana, and comminuting the at least one heat treated unpeeled banana to form a banana puree. The at least one banana is an (unripe) green banana, a (ripe) yellow banana, or combinations thereof.

Similarly, a method is provided for making a plantain product comprising providing at least one unpeeled plantain comprising plantain peel and plantain pulp, subjecting the at least one unpeeled plantain to a heat treatment at a temperature and for a time sufficient to gelatinize starch present in the at least one unpeeled plantain to form at least one heat treated unpeeled plantain, and comminuting the at least one heat treated unpeeled plantain to form a banana puree. The at least one plantain is an (unripe) green plantain, a (ripe) yellow plantain, a (overripe) black plantain, or combinations thereof.

It was discovered that when whole green bananas, whole green plantains, or whole yellow plantains are heat-treated through processes such as blanching in boiling water, a hot water shower, a steam shower, steam-parching, microwave heating, oven-baking, or frying, many advantages are created. For instance, the blanching of whole green bananas with boiling water for more than about ten minutes changes a plurality of properties of green banana: 1) to soften the peels such that they no longer require hand peeling; 2) to soften the whole green banana enough to be processed using conventional pureeing and pasteurizing systems without employing high feeding pump pressure; 3) to reduce the initial load of microorganisms present on the whole banana; 4) to gelatinize the starch in the peel and pulp to convert the fresh banana to a soft-solid consistency and undergo gelation after cooling to set edible gels; 5) to allow use of the high fiber peels; 6) to inactivate enzymatic browning reactions in the whole banana, to reduce astringency taste in the whole banana; and 7) to increase the whole banana viscosity due to gelation of starch. The same properties are changed upon heat treatment of green plantains or yellow plantains.

As used herein, the term "starch" refers to any polysaccharide comprising chains of monosaccharide molecules, including amylose and amylopectin. Amylose has an unbranched, linear, or spiral structure and amylopectin has a branched structure. When granules of starch are heated, they will swell upon absorption of moisture from the surrounding environment, and some granules will then collapse. Molecules of amylose and amylopectin will also escape from at least some of the starch granules. The collapsed starch granules, free amylose molecules, and free amylopectin molecules are thus available to associate with each other and form a gel network. As used herein, the terms "gelatinizing" and "gelatinization" refer to the process of converting a plurality of starch granules to a random arrangement of amylose and amylopectin molecules. Upon cooling, water (or other liquid) molecules are trapped in a network as the gel forms, which is referred to herein as "gelation".

The heat treatment employed to achieve gelatinization of the unpeeled bananas or plantains is not particularly limited, and for example includes contacting with boiling water, contacting with steam, contacting with hot water, contacting with hot oil, microwaving, contacting with hot air, and combinations thereof. For instance, the heat treatment according to certain aspects comprises blanching in boiling water, showering in hot water, subjecting to a steam shower (i.e., parching), microwave heating (e.g., at over 20 Watt-hours per kilogram of whole banana), oven baking, frying in oil, or combinations thereof.

In certain embodiments, the temperature of the heat treatment comprises at least 70 degrees Celsius and the time comprises at least ten minutes. In alternate embodiments, the temperature of the heat treatment comprises at least 80 degrees Celsius, or at least 90 degrees Celsius, or at least 100 degrees Celsius, or at least 110 degrees Celsius, or at least 120 degrees Celsius. In certain aspects, the time for the heat treatment comprises at least fifteen minutes, or at least twenty minutes, or at least twenty-five minutes, or at least thirty minutes, or at least thirty-five minutes, or at least forty minutes, or at least forty-five minutes, or at least fifty minutes, or at least fifty-five minutes, or at least one hour.

After subjection to one or more thermal processes, the stems are typically removed from the whole bananas or plantains and the heat treated whole banana or whole plantain is comminuted by any conventional blender, pureeing equipment, homogenization equipment, or the like until achieving a substantially homogeneous puree. According to certain embodiments of the invention, the heat treated whole banana or whole plantain may first be peeled, such as by using automatic banana peeling machines, prior to comminuting. In embodiments of the invention, the heat treated whole banana puree has a viscosity of at least about 5000 centipoises (cP), as measured by a controlled rate viscometer (e.g., an Anton Paar MCR Rheometer) with a 1 mm gap 2 degree cone-and-plate spindle at 0.01-100% strain range at 22 degrees Celsius. The comminuted (i.e., pureed) banana or plantain is optionally pasteurized using any commercial pasteurization equipment. In certain aspect, the ground banana or plantain is then packaged using any suitable packaging machine Depending on the intended use for the banana puree or plantain puree, the packaged banana puree or plantain puree is optionally chilled down to room temperature using cold air or water, thereby forming a soft solid structure, or stored before use at a temperature to inhibit microbial growth (i.e., about 4 degrees Celsius or less). When banana puree is cooled to set the gelatinized starch as a gel, the gel comprises a gel strength of at least about 600 gram (force) (i.e., about 5.88 newtons) when tested with a 1 inch diameter cylindrical probe.

Alternatively, the banana puree or plantain puree is converted to a powder or flake form. Banana or plantain powder and flake processing comprises dehydration of the banana or plantain puree by commercial dehydrators or dryers including for example and without limitation drum dryers, hot-air tunnel oven dryers, infra-red dryers, microwave dryers, reflectance-window dryers, or a combination of dryers. Typically, banana or plantain powder or flakes are dried to achieve a moisture content of below 10 weight %. After drying processes, the dried banana or plantain powder or flakes may be ground or sieved, based on the final application specifications.

In another aspect, a method is provided for making a banana product comprising providing at least one unpeeled banana comprising banana peel and banana pulp, subjecting the at least one unpeeled banana to a heat treatment to form at least one heat treated unpeeled banana, peeling the at least one heat treated unpeeled banana, and comminuting the at least one heat treated peeled banana to form a banana puree. In certain embodiments, the temperature comprises at least 70 degrees Celsius and the time comprises at least ten minutes. In certain aspects, the method further comprises drying the banana puree to form a banana powder.

In accordance with another aspect, a method is provided for making a plantain product comprising providing at least one unpeeled plantain comprising plantain peel and plantain pulp, subjecting the at least one unpeeled plantain to a heat treatment at a temperature and for a time sufficient to gelatinize starch present in the at least one unpeeled plantain to form at least one heat treated unpeeled plantain, and comminuting the at least one heat treated unpeeled plantain to form a plantain puree. The at least one plantain is an unripe green plantain, a ripe yellow plantain, an overripe black plantain, or combinations thereof. In certain embodiments, the temperature comprises at least 70 degrees Celsius and the time comprises at least ten minutes. In certain aspects, the method further comprises drying the plantain puree to form a plantain powder.

In another aspect, the invention relates to a functional food ingredient comprising a banana puree that comprises banana pulp and optionally banana peel. According to certain aspects the banana puree is dried and thereby provided in the form of a dried banana powder or flake. The functional food ingredient optionally performs as one or more of the following ingredient types: (1) a natural gluten substitute; (2) a natural gelling agent; (3) a natural fiber fortifying ingredient; (4) a texture modifier; (5) a viscosity enhancer; (6) a dispersing agent; (7) an emulsifying agent; (8) a dip and whip base for food, snack and beverage products; (9) a natural binder, (10) a bulking agent, (11) a sugar substitute, and combinations of any of them.

In at least certain embodiments, the functional food ingredient advantageously allows for reduction in the total amount of monosaccharides and/or disaccharides in a finished food product, for example achieving a reduction of up to about 25% by weight as compared to the finished food product without the functional food ingredient. Accordingly, heat treatment of whole unripe or ripe bananas provides a plurality of very useful functionalities for the banana puree, for example and without limitation, as a viscosity enhancer, a colloid/foam stabilizer, a binder, and a non-sweet bulking agent for dips, whips and sauces.

In another aspect, the invention relates to a functional food ingredient comprising a plantain puree that comprises plantain pulp and optionally plantain peel. According to certain aspects the plantain puree is dried and thereby provided in the form of a dried plantain powder or flake. The functional food ingredient optionally performs as one or more of the following ingredient types: (1) a natural gluten substitute, (2) a natural gelling agent, (3) a natural fiber fortifying ingredient, (4) a texture modifier, (5) a viscosity enhancer, (6) a dispersing agent, (7) an emulsifying agent, (8) a dip and whip base for food, snack and beverage products, (9) a natural binder, (10) a bulking agent, (11) a sugar substitute, and combinations of any of them.

Typically, a whole green banana comprises 78-82% moisture, 15-17% starch, <5% simple sugars, 1.5% protein, 0.5% fat, and 5% fiber including cellulose, α-glucan, pectin. Green banana flesh comprises a similar composition, with the most significant difference being that banana pulp does not comprise cellulose and thus contains about half of the total fiber as whole green bananas, i.e., 2.5% fiber. According to certain embodiments of the invention, the banana pulp comprises about 10% to 17% by weight starch, preferably resistant starch, which passes through the small intestine without undergoing digestion.

Typically, a whole green plantain comprises 60-70% moisture, 15-20% starch, <5% simple sugars, <1.5% protein, <0.5% fat, and 2.5-3.0% fiber, α-glucan, pectin. Green plantain flesh comprises a similar composition, with the most significant difference being that plantain pulp does not comprise cellulose and thus contains about half of the total fiber as whole green plantains, i.e., 2.5-3.0% fiber. According to certain embodiments of the invention, the plantain pulp comprises about 10% to 17% by weight starch, preferably resistant starch, which passes through the small intestine without undergoing digestion.

As noted above, green bananas have a higher content of starch and fiber and lower simple sugars than yellow bananas. Similarly, green plantains and yellow plantains have a higher content of starch and fiber and lower simple sugar content than overripe plantains. Due to the high content of starch and fiber, each of green banana puree, green plantain puree, and yellow plantain puree, provides very unique functionalities such as a viscosity enhancer, gelling agent, fiber enhancer, gluten replacer, foam stabilizer, emulsion stabilizer, sugar replacer, and natural volumetric bulking agent, and further provides a bland taste. Moreover, the high fiber content of the peel provides functional benefits beyond that of banana or plantain pulp alone. In addition, the employment of unpeeled banana or plantain puree or powder provides the further benefit of minimizing waste by using whole fruits, due to the pureeing of whole bananas or whole plantains including both the peels and flesh.

Accordingly, the inventive banana puree comprising banana pulp and preferably also banana peel, or the inventive plantain puree comprising plantain pulp and preferably also plantain peel, is advantageously employed as a functional food ingredient, wherein the function is for example and without limitation, a vegan whip base, a natural gelating agent, a fiber fortifying ingredient, a texture modifier, a viscosity enhancer, a dispersing agent, an emulsifying agent, a natural binder, and combinations thereof. The functional food ingredient is added to a food product for example and without limitation, a snack food, a baked product, a pasta, a squeezable wet food (e.g., whole fruit puddings, fruit toppings, and the like), a spoonable wet food, a beverage, a dip, a whip, a sauce, a salad dressing, shelf stable multi-textured snacks and mini-meals (e.g., cookie and cracker sandwiches with 100% fruit fillings, food wraps, etc.) and combinations thereof.

Moreover, it has been discovered that plants of the genus *Musa*, including bananas and plantains, contain valuable components having the potential to act as phytonutrients, such as antioxidants. The article "High valuable compounds from the unripe peel of several *Musa* species cultivated in Madeira Island (Portugal)", Juan Jose Villaverde et al., Industrial Crops and Products, 2013, vol. 42, pp. 507-512, reports that gas chromatography-mass spectrometry analyses of lipophilic extracts of unripe peel of ten different *Musa* cultivars identified sterols (including cycloeucalenone) and fatty acids as the major families of compounds in the extracts (see Abstract). Similarly, the article "Antioxidant Potential of Peel Extracts of Banana Varieties (*Musa sapientum*)", Ramakrishnan Baskar et al., Food and Nutrition Sciences, 2011, vol. 2, pp. 1128-1133, discloses spectrophotometric analyses of flavonoids and total polyphenols in ethanolic extracts of the peel of nine different *Musa* varieties, as well as free radical scavenging capacity of the peel extracts (see Abstract). In particular, the Baskar et al. article reports that the extracts of naturally ripened peels exhibited free radical scavenging activity in each of the varieties, although to different extents (see page 1131). The ethanolic extracts all contained flavonoids and phenols, and the Baskar et al. article concludes that "the relationship between phytochemical content and free radical scavenging activity of banana peel indicates that peel extracts from these varieties may be useful to combat free radical mediated diseases." (page 1132) Accordingly, the employment of whole heat treated bananas and/or plantains in food and beverage products potentially has the further advantage of providing the health benefits associated with consuming sterols, fatty acids, and phytochemicals.

An aspect of the invention provides a gluten substitute comprising a banana puree, wherein the banana puree comprises banana peel and banana pulp. The banana puree preferably comprises unripe bananas. Another aspect of the invention provides a gluten substitute comprising a plantain puree, wherein the plantain puree comprises plantain peel and plantain pulp. The plantain puree preferably comprises unripe plantains. An additional aspect of the invention provides a comestible comprising the gluten substitute. The comestible is, for example and without limitation, a snack food, a baked product, a pasta, a squeezable wet food, a spoonable wet food, a beverage, a dip, a whip, a sauce, a salad dressing, and combinations thereof.

An embodiment of the invention provides a method for making a banana product comprising providing at least one unpeeled green banana comprising banana peel and banana pulp, subjecting the at least one unpeeled banana to a heat treatment at a temperature and for a time sufficient to gelatinize starch present in the at least one unpeeled banana to form at least one heat treated unpeeled banana, peeling the at least one heat treated unpeeled banana, and comminuting the banana pulp of the at least one heat treated peeled banana to form a banana puree. Preferably, the banana comprises at least one unripe banana.

A further embodiment of the invention provides a method for making a plantain product comprising providing at least one unpeeled green plantain comprising plantain peel and plantain pulp, subjecting the at least one unpeeled plantain to a heat treatment at a temperature and for a time sufficient to gelatinize starch present in the at least one unpeeled plantain to form at least one heat treated unpeeled plantain, peeling the at least one heat treated unpeeled plantain, and comminuting the plantain pulp of the at least one heat treated peeled plantain to form a plantain puree. Preferably, the plantain comprises at least one unripe plantain.

In a further aspect, the invention relates to a snack bar comprising grains, fruit juice, and at least one of green banana powder, green banana puree, green plantain powder, green plantain puree, yellow plantain powder, and yellow plantain puree. The one or more grains are selected from the group consisting of oat, wheat, corn, rice, barley, millet, sorghum, rye, triticale, teff, wild rice, spelt, buckwheat, amaranth, quinoa, kaniwa, cockscomb, and combinations thereof. The snack bar may further comprise at least one particulate selected from the group consisting of chocolate chips, nuts, fruit pieces, and combinations thereof.

According to certain embodiments, the snack bar comprises a granola bar and the powder or puree is included at least in the binder that assists to hold the individual grains and other solid ingredients together. The use of banana or plantain powder, for example, can eliminate the need for one or more non-natural ingredients typically included in snack bar binders, such as partially hydrogenated oils. Moreover, the combination of naturally sweet fruit juice (e.g., fruit juice concentrate) and banana or plantain powder or puree can eliminate the need for any refined sugars, corn syrups, or other added sweeteners to be included in the snack bar binder. An advantage of employing a snack bar binder comprising fruit juice and banana powder is a significant decrease in total calories (e.g., by 10%), calories from fat (e.g., by 25%), total fat (e.g., by 50%), and saturated fat (e.g., by 33%), as compared to a typical snack bar comprising ingredients such as corn syrup, invert sugar, sugar, corn syrup solids, and partially hydrogenated oil.

Adjusting the ratios of fruit juice and banana or plantain powder or puree allows for optimization of properties of the finished snack bar. For instance, including greater amounts of banana powder increases the final viscosity of the binder. In at least certain embodiments of the invention, the binder exhibits a viscosity of between about 2 Pascales-seconds (Pa·s) and about 8 Pa·s, measured at 60 rotations per minute (rpm) of shear, at the time of mixing the binder with the snack bar particulates. Following coating and cooling, the binder exhibits a high yield stress measured at 0 rpm of shear. The viscosity may be measured using the ASTM WK31279 test method, employing either a Brookfield rotary viscometer method or a rheometer method. ASTM WK31279 takes into account the viscometer geometry, temperature, and rotation speed. Viscosity is determined from the slope of the shear stress and strain, while the yield stress is determined from the extrapolation of the stress and strain curve to 0 rpm to obtain the Y-intercept value, which is the imaginary stress at a strain value of 0.

According to certain embodiments, a snack bar binder comprises between about 5 wt. % and about 20 wt. % of the at least one of green banana powder, green banana puree, green plantain powder, green plantain puree, yellow plantain powder, and yellow plantain puree. The binder for a snack bar also optionally comprises glycerine (also interchangeably referred to as "glycerol" or "glycerin"), for example in an amount between about 2 wt. % and about 15 wt. %, or between about 5 wt. % and about 12 wt. %. Glycerine is typically added to decrease the water activity of the snack bar and to slow the gel formation process of the binder as it cools.

In certain embodiments, the water activity ($A_w$) of the snack bar ranges from about 0.30 to about 0.60, such as from about 0.35 to about 0.45. In certain embodiments, the water activity of the snack bar binder ranges from about 0.40 to about 0.70, such as from about 0.45 to about 0.60. Both the heat treated banana and/or plantain product and any optional glycerine present act to reduce the water activity of a binder and snack bar as compared to the same binder and bar without the heat treated banana and/or plantain product (and optional glycerine).

Juices suitable for use in at least certain exemplary embodiments of the invention disclosed here include, e.g., fruit, vegetable and berry juices. Juices can be employed in the present invention in the form of a single-strength juice, NFC juice, 100% pure juice, clarified juice, juice concentrate, juice puree, or other suitable forms. The term "juice" as used here includes single-strength fruit, berry, or vegetable juice, as well as concentrates, purees, milks, and other forms. Multiple different fruit, vegetable and/or berry juices can be combined, optionally along with other flavorings, to generate a product having the desired flavor.

Examples of suitable juice sources include orange, lemon, lime, tangerine, mandarin orange, tangelo, pomelo, grapefruit, white grape, red grape, sweet potato, tomato, celery, beet, lettuce, spinach, cabbage, watercress, rhubarb, carrot, cucumber, raisin, cranberry, pineapple, peach, banana, apple, pear, guava, apricot, watermelon, Saskatoon berry, blueberry, plains berry, prairie berry, mulberry, elderberry, Barbados cherry (acerola cherry), choke cherry, date, coconut, olive, raspberry, strawberry, huckleberry, loganberry, currant, dewberry, boysenberry, kiwi, cherry, blackberry, quince, buckthorn, passion fruit, sloe, rowan, gooseberry, pomegranate, persimmon, mango, rhubarb, papaya, lychee, plum, prune, date, currant, fig, etc. Numerous additional and alternative juices suitable for use in at least certain exemplary embodiments will be apparent to those skilled in the art given the benefit of this disclosure.

In a further aspect, the invention relates to a cracker comprising at least one whole grain flour; starch; baking powder; and at least one of green banana powder, green banana puree, green plantain powder, green plantain puree, yellow plantain powder, and yellow plantain puree, for example green banana powder comprising green banana peel and green banana pulp. Optionally, the cracker further comprises sweetening provided by refined sweeteners, fruits, or combinations thereof. Nonlimiting examples of refined sweeteners include sucrose, corn syrup, invert sugar, corn syrup solids, glycerine, and combinations thereof. Nonlimiting examples of fruits include fruit juice, fruit juice concentrate, fruit puree, dried fruit, and combinations thereof. The starch is provided by any suitable starch, including without limitation cornstarch, tapioca, wheat starch, potato starch, a modified starch, a waxy starch, and combinations thereof. A skilled practitioner will be capable of identified additional suitable minor ingredients to include in a cracker product, from benefit of this disclosure. The heat treated banana and/or plantain acts in the cracker in the capacity of at least one of a texture modifier, a natural binder, a fiber fortifying agent, a bulking agent, and a sugar substitute.

In yet a further aspect, the invention relates to a cereal comprising grains and at least one of green banana powder, green banana puree, green plantain powder, green plantain puree, yellow plantain powder, and yellow plantain puree. The cereal optionally comprises an instant oatmeal or a ready to eat cereal. According to certain embodiments, the at least one grain is selected from the group consisting of oat, wheat, corn, rice, barley, millet, sorghum, rye, triticale, teff, wild rice, spelt, buckwheat, amaranth, quinoa, kaniwa, cockscomb, and combinations thereof.

Instant oatmeal typically comprises oat grain selected from the group consisting of whole rolled oat flakes, steel cut oat flakes, oat flake pieces, whole oat flakes, and combinations thereof. In certain embodiments, instant oatmeal comprises other dry ingredients, including sucrose, salt, flavors, spices, dried fruit, nuts, oat flour, vitamins and minerals. The heat treated banana and/or plantain acts in the instant oatmeal in the capacity of at least one of a texture modifier, a viscosity enhancer, a dispersing agent, a natural binder, a fiber fortifying agent, a bulking agent, and a sugar substitute.

Ready to eat (RTE) cereal pieces typically comprise a source of a suitable flour mixture containing any suitable flour as desired, such as oat flour, wheat flour, corn flour and mixtures thereof, as well as other flours, grains and mixtures thereof. The flour mixture may also include sugar in any suitable form such as molasses, unsulphured molasses, honey, sucrose, or other suitable sugars and mixtures thereof. The at least one green banana powder, green banana puree, green plantain powder, green plantain puree, yellow plantain powder, and yellow plantain puree advantageously acts as a bulking agent, among other functions, thus a reduced amount of sugar is employed compared to RTE cereal pieces without the heat treated banana and/or plantain. The flour mixture may also include other natural and/or artificial materials, including salt, additional flavors, vitamins and minerals as desired. In an embodiment, the RTE cereal pieces are prepared from a dough comprising the flour mixture, the heat treated banana and/or plantain, and water. Typically, cereal dough is cooked and flaked or extruded and cut into pieces, as well known to the skilled practitioner. The heat treated banana and/or plantain acts in the RTE cereal in the capacity of at least one of a texture modifier, a natural binder, a fiber fortifying agent, a bulking agent, and a sugar substitute.

In another aspect, the invention relates to a smoothie comprising fruit selected from the group consisting of fruit juice, dried fruit, fresh fruit, frozen fruit, fruit puree, and combinations thereof, and at least one of green banana powder, green banana puree, green plantain powder, green plantain puree, yellow plantain powder, and yellow plantain puree. Smoothies are a popular class of beverages in the United States, typically comprising a variety of ingredients which are blended together to form a fresh, unique and healthy snack. Smoothies are known for their thick, rich mouthfeel and often employ cream, fruit, juice, dairy, soy, vegetable, vitamin and fiber components. As used herein, the term "smoothie" particularly refers to a beverage with a characteristic thickness which can be attributed to the presence therein of ingredients such as sweeteners, acids, vitamins, fiber, fruit juice, fruit puree, milk, milk solids, milk proteins, soy milk, soy proteins, coffee, coffee solids, vegetable juice, vegetable puree, tea, tea solids, preservatives, buffers, colors, flavors, and combinations thereof. Smoothie beverages may be fruit-based, juice-based, dairy-based, coffee-based, soy-based, vegetable-based, tea-based or a combination thereof. The heat treated banana and/or plantain acts in smoothies in the capacity of at least one of a texture modifier, a viscosity enhancer, a dispersing agent, an emulsifying agent, a bulking agent, a natural gelling agent, a natural fiber fortifying ingredient, and a sugar substitute.

In yet a further aspect, the invention relates to a cookie comprising flour, shortening, at least one sweetener, and at least one of green banana powder, green banana puree, green plantain powder, green plantain puree, yellow plantain powder, and yellow plantain puree. A batter is prepared by combining, for example, whole grains, leavening agents, texturizing agents, flour, sugar, emulsifiers, and proteins, to form a dry mixture. Water, shortening, and other moist ingredients are added to the dry mixture to form a batter. The heat treated banana and/or plantain acts in the cookies in the capacity of at least one of a texture modifier, a natural binder, a dispersing agent, a fiber fortifying agent, a bulking agent, and a sugar substitute.

Suitable leavening agents include, but are not limited to, baking powder, baking soda, monocalcium phosphate, potassium bitatrate (cream of tartar) and the like. Suitable amounts of acids, such as citric acid, are about 0.1% to about 0.4 wt % based on total weight of the batter. Suitable texturizing agents include starches, modified starches (e.g gelatinized starches), gum acacias, alginates, carrageenans, carboxymethylcellulose, gelatin, guar gum, locust bean gum, pectin, and xanthan gum. The texturizing agents systems are used in amounts to produce the proper level of cake moistness and density through proper water adsorption. Suitable amounts of texturizing agents are about 0.1% to about 0.4 wt % based on total weight of the batter. Suitable flours include, but are not limited to, cake flour, wheat flour, corn flour, and oat flour. Suitable sugars include, but are not limited to, white sugar and brown sugar. Suitable proteins include, but are not limited to, eggs, egg whites, sodium caseinate, whey, wheat gluten, and the like. Fruit pieces or nuts or chips such as chocolate chips or butterscotch chips, for example, may be included. Flavors, colors, and other minor components also may be added. Non-mineral nutritive compounds such as vitamins can be added to the cookies. Examples of non-mineral nutritional supplement ingredients are known to those of ordinary skill in the art and include, for example, antioxidants and vitamins, including Vitamins A, D, E (tocopherol), C (ascorbic acid), B1 (thiamine), B2 (riboflavin), B6, B12, and K, niacin, folic acid, biotin, and combinations thereof.

The ability of the heat treated banana and plantain products to act as sugar replacers means that in certain food and beverage products a potent sweetener may be added to make up for the sweetness lost by replacing some or all of the sugar. As used herein, a "potent sweetener" means a sweetener which is at least twice as sweet as sugar, that is, a sweetener which on a weight basis requires no more than half the weight of sugar to achieve an equivalent sweetness. For example, a potent sweetener may require less than one-half the weight of sugar to achieve an equivalent sweetness in a beverage sweetened to a level of 10 degrees Brix with sugar. Potent sweeteners include both nutritive (e.g., Lo Han Guo juice concentrate) and non-nutritive sweeteners (e.g., typically, Lo Han Guo powder). In addition, potent sweeteners include both natural potent sweeteners (e.g., steviol glycosides, Lo Han Guo, etc.) and artificial potent sweeteners (e.g., neotame, etc.). However, for natural food and beverage products disclosed here, only natural potent sweeteners are employed. As used herein, a "non-nutritive sweetener" is one which does not provide significant caloric content in typical usage amounts, e.g., is one which imparts less than 5 calories per 8 oz. serving of beverage to achieve the sweetness equivalent of 10 Brix of sugar.

Sweeteners suitable for use in various embodiments of the food and beverage products disclosed herein include nutritive and non-nutritive, natural and artificial or synthetic sweeteners. Suitable sweeteners and combinations of sweeteners are selected for the desired nutritional characteristics, functional characteristics, taste profile, mouthfeel and other organoleptic factors. Non-nutritive artificial sweeteners suitable for at least certain exemplary embodiments include, for example, peptide based sweeteners, e.g., aspartame, neotame, and alitame, and non-peptide based sweeteners, for example, sodium saccharin, calcium saccharin, acesulfame (including but not limited to acesulfame potassium), cyclamate (including but not limited to sodium cyclamate and/or calcium cyclamate), neohesperidin dihydrochalcone, and sucralose. Alitame may be less desirable for caramel-containing beverages where it has been known to form a precipitate. In certain exemplary embodiments the beverage product employs aspartame as the sweetener, either alone or with other sweeteners. In certain other exemplary embodiments the sweetener comprises aspartame and acesulfame potassium. Other non-nutritive sweeteners suitable for at least certain exemplary embodiments include, for example, sorbitol, mannitol, xylitol, glycyrrhizin, neohesperidin dihydrochalcone, D-tagatose, erythritol, meso-erythritol, malitol, maltose, lactose, fructo-oligosaccharides, Lo Han Guo powder, steviol glycosides, e.g., rebaudiosides such as Rebaudioside A, Rebaudioside D, stevioside, etc., xylose, arabinose, isomalt, lactitol, maltitol, trehalulose, and ribose, and protein sweeteners such as monatin, thaumatin, monellin, brazzein, L-alanine and glycine related compounds and mixtures of any of them. Lo Han Guo, steviol glycosides, e.g., rebaudiosides such as Rebaudioside A, Rebaudioside D, stevioside, etc. and related compounds, as discussed further below, are natural non-nutritive potent sweeteners. It will be within the ability of those skilled in the art, given the benefit of this disclosure, to select suitable non-nutritive sweeteners (e.g., one or combination of non-nutritive sweeteners, either alone or together with nutritive sweetener) for a particular embodiment of the food and beverage products disclosed here.

In at least certain exemplary embodiments of the food and beverage products disclosed here, the sweetener component can include nutritive, natural crystalline or liquid sweeteners such as sucrose, liquid sucrose, fructose, liquid fructose, glucose, liquid glucose, leucrose, trehalose, galactose, isomaltulose, dextrose, maltodextrin, corn syrup solids, glucooligosaccharides, glucose-fructose syrup from natural sources such as apple, chicory, honey, etc., e.g., high fructose corn syrup, invert sugar, maple syrup, maple sugar, honey, brown sugar molasses, e.g., cane molasses, such as first molasses, second molasses, blackstrap molasses, and sugar beet molasses, sorghum syrup and/or others. Such sweeteners are present in at least certain exemplary embodiments in an amount of from about 0.1% to about 20% by weight of the product, such as from about 1% to about 4% by weight, depending upon the desired level of sweetness for the finished product. To achieve desired uniformity, texture and taste, in certain exemplary embodiments of the natural products disclosed here, standardized liquid sugars as are commonly employed in the food and beverage industry can be used. Typically such standardized sweeteners are free of traces of nonsugar solids which could adversely affect the flavor, color or consistency of the finished product.

Non-nutritive, high potency sweeteners typically are employed at a level of milligrams per fluid ounce of beverage, or per dry ounce of food, according to their sweetening power, any applicable regulatory provisions of the country where the beverage is to be marketed, the desired level of sweetness of the beverage, etc. It will be within the ability of those skilled in the art, given the benefit of this disclosure, to select suitable additional or alternative sweeteners for use in various embodiments of the food and beverage products disclosed here.

As mentioned above, at least certain exemplary embodiments of the food and beverage products disclosed here employ a sweetening amount of one or more steviol glycosides, e.g., rebaudiosides such as Rebaudioside A, Rebaudioside B, Rebaudioside C, Rebaudioside D, Rebaudioside E, Rebaudioside F, stevioside, etc. or related compounds or mixtures of any of them for sweetening. These compounds can be obtained by extraction or the like from the *stevia* plant. *Stevia* (e.g., *Stevia rebaudiana bectoni*) is a sweet-tasting plant. The leaves contain a complex mixture of natural sweet diterpene glycosides. Steviol glycosides, e.g., rebaudiosides such as Rebaudioside A, stevioside, etc. are components of *Stevia* that contribute sweetness. Typically, these compounds are found to include stevioside (4-13% dry weight), steviolbioside (trace), the rebaudiosides, including rebaudioside A (2-4%), rebaudioside B (trace), rebaudioside C (1-2%), rebaudioside D (trace), and rebaudioside E (trace), and dulcoside A (0.4-0.7%). The following nonsweet constituents also have been identified in the leaves of *stevia* plants: labdane, diterpene, triterpenes, sterols, flavonoids, volatile oil constituents, pigments, gums and inorganic matter. In at least certain embodiments of the food and beverage products disclosed herein, non-nutritive sweeteners steviol glycosides, e.g., rebaudiosides such as Rebaudioside A, stevioside, etc. may be included in finished compositions at a weight percent of about 0.01% to about 10.0%, and preferably between about 0.02% and about 0.75%.

The sweetener Lo Han Guo, which has various different spellings and pronunciations and is abbreviated here in some instances as LHG, can be obtained from fruit of the plant family Cucurbitaceae, tribe Jollifieae, subtribe Thladianthinae, genus *Siraitia*. LHG often is obtained from the genus/species *S. grosvenorii, S. siamensis, S. silomaradjae, S. sikkimensis, S. africana, S. borneensis*, and *S. taiwaniana*. Suitable fruit includes that of the genus/species *S. grosvenorii*, which is often called Lo Han Guo fruit. LHG contains triterpene glycosides or mogrosides, which constituents may be used as LHG sweeteners. Lo Han Guo is a potent sweetener which can be provided as a natural nutritive or natural non-nutritive sweetener. For example, Lo Han Guo juice concentrate may be a nutritive sweetener, and Lo Han Guo powder may be a non-nutritive sweetener. Lo Han Guo can be used as the juice or juice concentrate, powder, etc. Preferably LHG juice contains at least about 0.1%, e.g., from 0.1% to about 15%, mogrosides, preferably mogroside V, mogroside IV, (11-oxo-mogroside V), siamenoside and mixtures thereof. LHG can be produced, for example, as discussed in U.S. Pat. No. 5,411,755. Sweeteners from other fruits, vegetables or plants also may be used as natural or processed sweeteners or sweetness enhancers in at least certain exemplary embodiments of the food and beverage products disclosed here.

EXAMPLES

Example 1

Green banana puree samples were prepared and tested for their viscoelastic properties. The green banana purees were compared to a yellow banana puree as a control. The whole green bananas were subject to different conditions, including heat treatment and/or peeling, followed by pureeing. The resulting purees are shown in FIG. 1.

The green bananas that were subjected to heat treatment were whole (i.e., unpeeled) and soaked in boiling water at 100° C. for 10 to 20 minutes, and then either peeled to provide only banana pulp, or left unpeeled. The fresh green bananas were either peeled to provide only banana pulp, or left whole. Last, the bananas, (i.e., peeled, whole, fresh and/or heat treated) were subjected to pureeing in a conventional high speed blender (e.g., VitaMix) until achieving a substantially homogeneous puree.

Figure 1B:
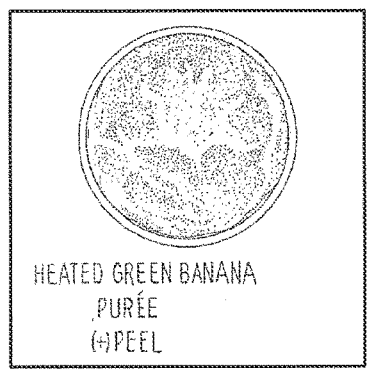
FIG. 1b shows heat treated green banana puree pulp with peel.
Figure 1C:
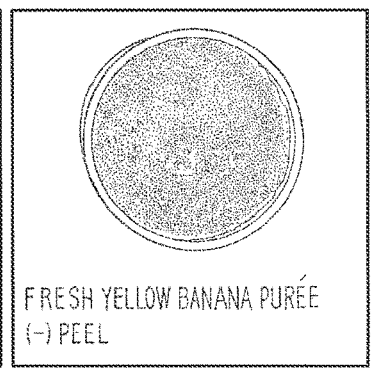
FIG. 1c shows fresh yellow banana puree pulp (without peel).
Figure 1D:
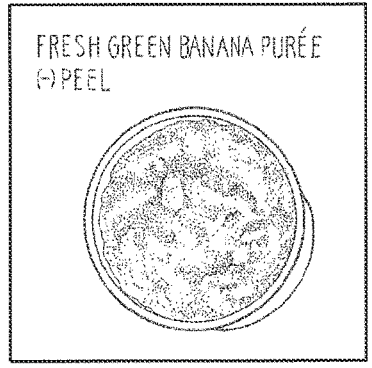
FIG. 1d shows fresh green banana puree pulp (without peel).
Figure 1E:
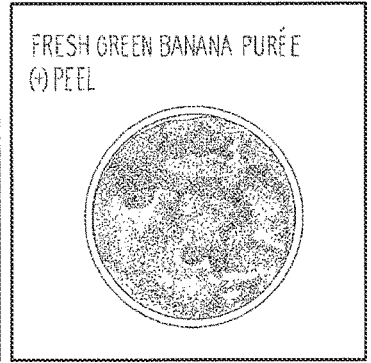
FIG. 1e shows fresh green banana puree pulp with peel.

FIG. 1a shows heat treated green banana pulp puree, which exhibited a very pale cream color. FIG. 1b shows heat treated whole green banana puree, which exhibited a pale yellow color with dark specs distributed throughout the puree. FIG. 1c shows a control banana puree, namely fresh yellow banana pulp puree, which exhibited a light brown color, and FIG. 1d shows fresh green banana pulp puree, which also exhibited a light brown color. FIG. 1e shows fresh whole green banana puree, which exhibited a medium brown color. Accordingly, the heat treatment of green bananas, both whole and peeled to provide only banana pulp, prevents enzymatic browning of the banana puree. Moreover, it is clear (e.g., from FIG. 1) that banana peel contributes to color of banana puree, particularly if the whole bananas have not been subjected to heat treatment.

Figure 2:
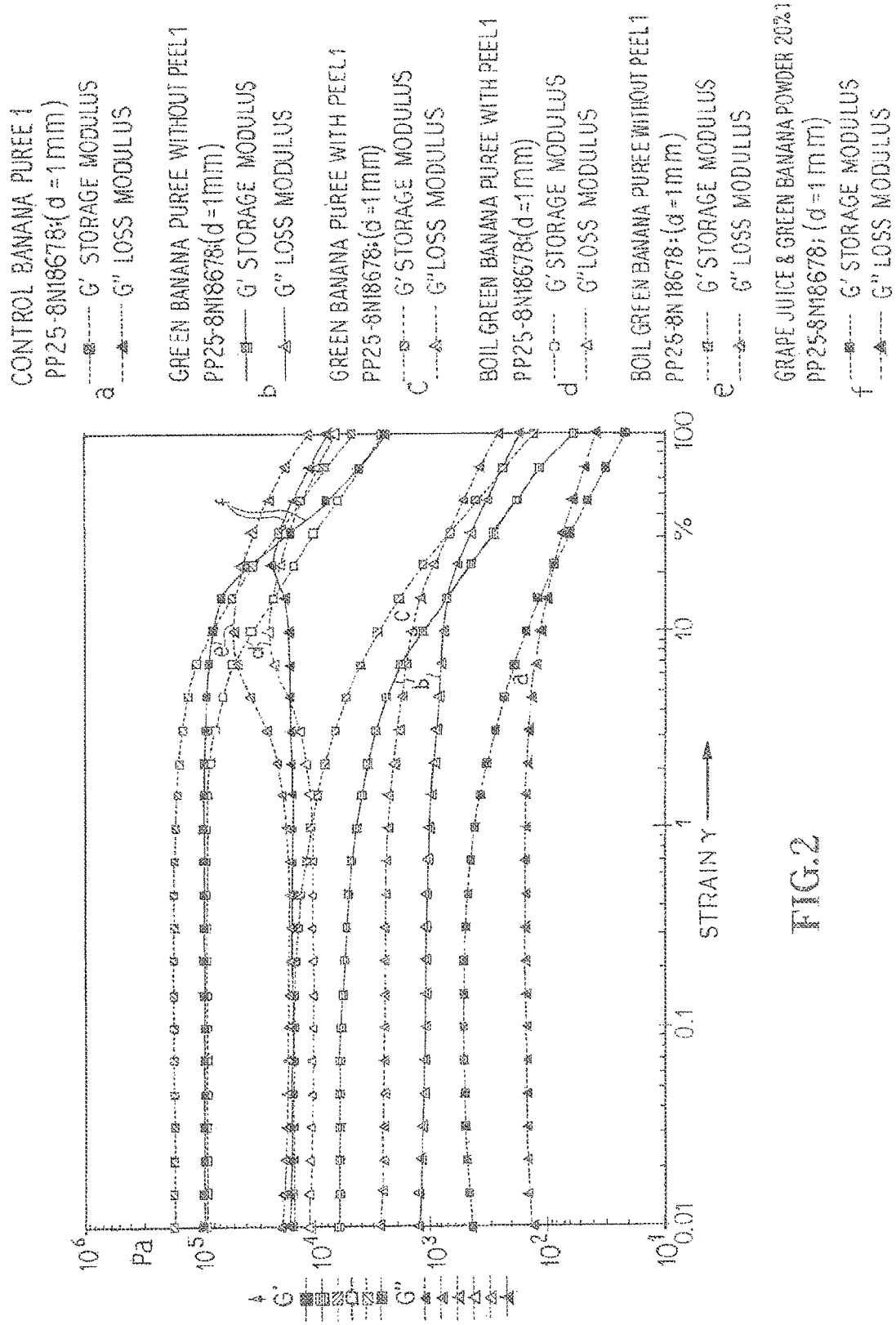
FIG. 2 provides a graph of the viscoelastic properties of green banana puree with and without peels.

Viscoelastic properties of the banana puree samples were tested on an Anton Paar dynamic mechanical analyzer using simplified ASTM E2254 and a rheometer (Anton Paar USA Inc., Ashland, Va.) and the results are shown in FIG. 2. The tests were performed using a gap distance of 1 millimeter (mm), a parallel dimension spindle, an angular frequency (omega) of 10 rad/sec, a temperature of 22° C., and an amplitude (gamma) of 0.1 to 100% of the 1 millimeter gap. The measured storage modulus and loss modulus values demonstrate that the heat treatment of green bananas increases the gel strength of banana puree, both with and without peels.

For example, FIG. 2 shows that both the storage modulus and the loss modulus of boiled green banana puree, either whole or peeled, are at least $10^4$ at a strain between 0.01 and 1 $sec^{-1}$. In contrast to the heat treated green banana puree, each of fresh yellow banana pulp puree and fresh green banana pulp puree exhibited measured storage modulus and loss modulus values of less than $10^4$ at a strain between 0.01 and 1 $sec^{-1}$. Only fresh green whole banana puree had a storage modulus of greater than $10^4$ at a strain between 0.01 and 1 $sec^{-1}$, thus clearly the presence of peel increases viscoelastic properties of banana puree.

Example 2

Viscosity of the banana purees prepared in Example 1 was tested using a rapid visco analyzer and the measured viscosities are provided below in Table 1. The experimental conditions follow Newport Scientific Method ST-00 (General method for testing starch in the Rapid Visco Analyzer). Total sample amounts in the test can were 28 grams, including water and the dry powder of the puree. The viscosity values demonstrate that the heat treatment increases the viscosity of the banana puree, as does the inclusion of banana peel. For instance, the peak viscosity of green banana pulp increased from 8121 centipoises (cP) for fresh green banana pulp to 9158 cP for heat treated green banana pulp. Without wishing to be bound by theory, it is believed that the lower viscosity of the heated whole green banana puree relative to that of the unheated banana puree is the result of cell structure changes and starch gelatinization that occurred as a result of heating. All of the viscosity values for the green banana purees were significantly higher than those for commercially available green banana pulp powder (Confoco) and yellow banana pulp powder (Gerber®).

TABLE 1

Viscosity of various banana purees using a rapid visco analyzer.

| Banana Material | Peak Viscosity (cP) | Peak Temp. (° C.) | Hold Viscosity (cP) | Final Viscosity (cP) | Pasting Temp. (° C.) |
|---|---|---|---|---|---|
| Fresh Green Pulp | 8121 | 95 | 3573 | 9714 | 77.1 |
| Fresh Whole Green | 9399 | 95 | 4285 | 9353 | 77.2 |
| Heat Treated Green Pulp | 9158 | 78 | 3204 | 5187 | 58.3 |
| Heat Treated Whole Green | 5323 | 77 | 990 | 2126 | 58.4 |
| Confoco Green Pulp Powder | 583 | 95 | 482 | 822 | 20.0 |
| Gerber ® Yellow Pulp Powder | 126 | 25 | 98 | 162 | N/A |

Example 3

The texture profile of two replicates of heat treated whole green banana puree prepared in Example 1 was tested. The texture profile analysis (TPA) of the green banana puree sample was measured by a Texture Analyzer (i.e., TA.XT. Plus). The sample was filled into TA-425 as a holder. The probe used was an acrylic cylinder with a 25.4 mm diameter, and the stress area was 490.87 $mm^2$. The cylinder probe was programmed to penetrate the samples to a depth of 6 mm at a rate of 10 mm/s and with a trigger force of 5.0 grams (0.049 newtons). The average measured texture attributes are provided below in Table 2.

TABLE 2

Texture profile analysis of heat treated whole green banana puree.

| Sample | Texture (Ave.) | Standard Deviation | Coefficient of Variation (%) |
|---|---|---|---|
| Force (g force) | 630.009 | 23.672 | 3.757 |
| Hardness (g) | 685.295 | 43.719 | 6.38 |
| Adhesiveness (g · sec) | −606.712 | 77.32 | −12.744 |
| Springiness | 0.967 | 0 | 0 |
| Cohesiveness | 0.793 | 0.025 | 3.19 |
| Gumminess | 542.567 | 17.323 | 3.193 |
| Chewiness | 524.395 | 16.743 | 3.193 |
| Resilience | 0.035 | 0.001 | 3.504 |

Example 4

Heat treated whole green banana puree prepared according to Example 1 was tested for its capacity to disperse ingredients, following dilution and whipping with water. The capacity for dispersion was compared with egg whites and an egg white and water system.

Figure 3D:
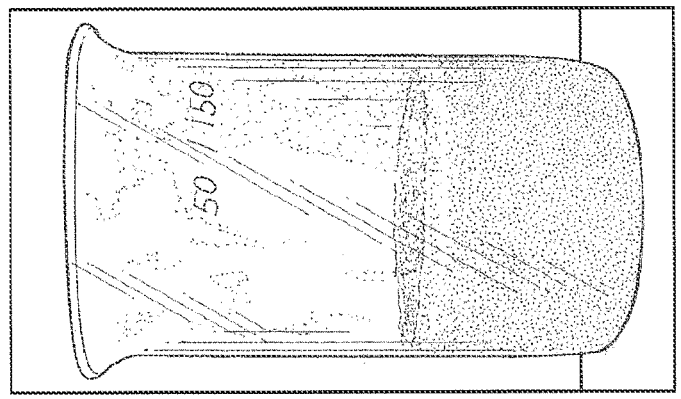
FIG. 3d shows whipped heat treated whole green banana puree (25%) in water (75%).
Figure 3C:
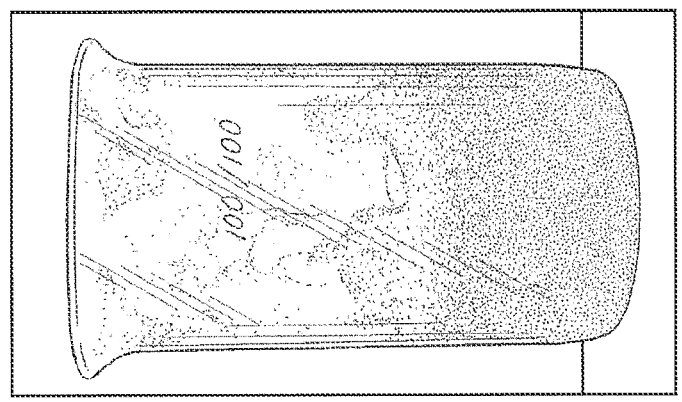
FIG. 3c shows whipped heat treated whole green banana puree (50%) in water (50%).
Figure 3B:
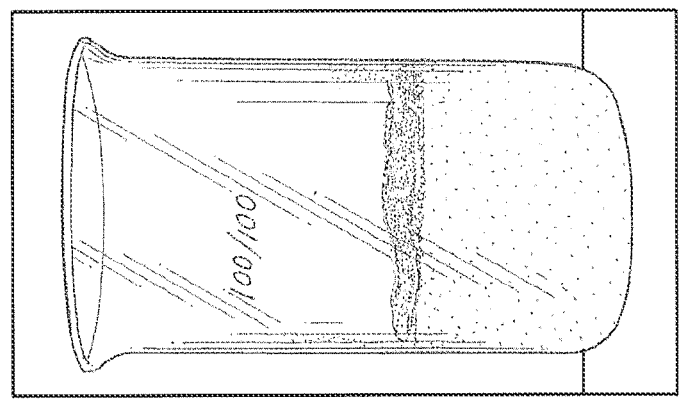
FIG. 3b shows whipped egg white (50%) in water (50%).
Figure 3A:
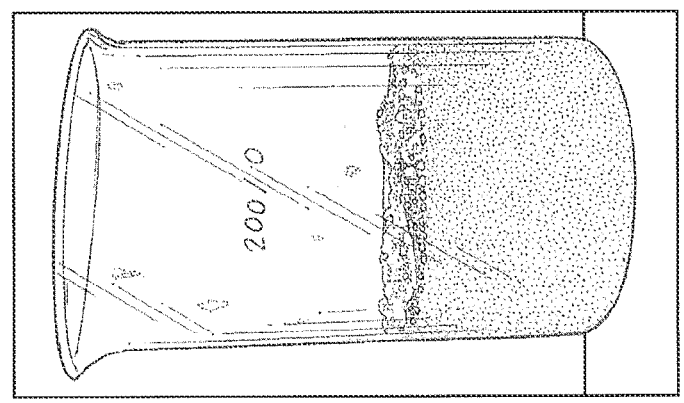
FIG. 3a shows whipped egg white.

Referring to FIG. 3a, egg whites were whipped in a beaker using an Oster 2-speed hand held mixer for approximately 2 minutes until a homogeneous appearance was achieved, then allowed to sit undisturbed for three hours. The appearance of the whipped egg whites remained homogeneous, with some foam present on top of the egg white surface. FIG. 3b shows a mixture of 50% by weight egg whites and 50% by weight water whipped in a beaker (i.e., under the same conditions as the 100% egg white sample of FIG. 3a) and allowed to sit undisturbed for three hours. The appearance of the 50/50 mixture of egg whites and water also remained homogeneous and included foam on the system surface.

FIG. 3c shows a mixture of 50% by weight heat treated whole green banana puree and 50% by weight water whipped in a beaker using an Oster 2-speed hand held mixer for approximately 2 minutes until a homogeneous appearance was achieved and then allowed to sit undisturbed for three hours. The appearance of the 50/50 mixture of heat treated whole green banana puree and water remained homogeneous without any phase separation or sedimentation. FIG. 3d shows a mixture of 25% by weight heat treated whole green banana puree and 75% by weight water whipped in a beaker until a homogeneous appearance was achieved and then allowed to sit undisturbed for three hours. The appearance of the 25/75 mixture of heat treated whole green banana puree and water also remained homogeneous without any phase separation or sedimentation, but with some foam present on the surface of the system. Accordingly, heat treated whole green banana puree is at least as capable of maintaining the dispersion of ingredients in a water mixture as egg whites.

Example 5

Heat treated whole green banana puree prepared according to Example 1 was tested for its capacity to act as a dip base, including consistency. The puree samples were compared to dip bases comprising cream cheese and chickpea paste. The texture profiles of the sample dips were tested, and the measured texture attributes are provided below in Table 3. The whipped products comprising banana puree generally exhibited higher texture analysis values than corresponding products with cream, cheese or chickpea, which provides an indication that considerably lower amounts of the banana puree is needed to achieve comparable texture consistencies of similar traditionally whipped products.

Figure 4A:
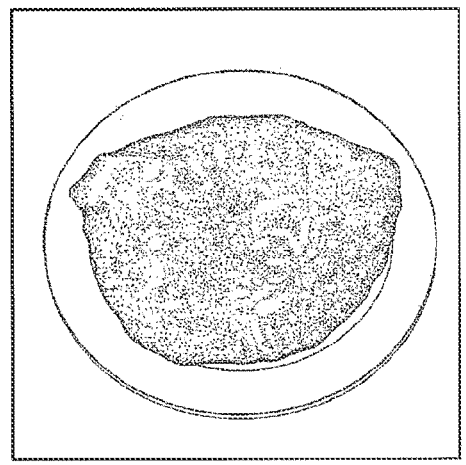
FIG. 4a shows a heat treated green banana based dip with milk.
Figure 4B:
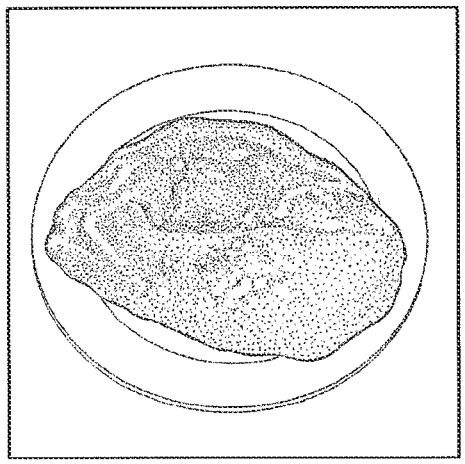
FIG. 4b shows a control dip containing cream cheese and milk.

Referring to FIG. 4a, a green banana puree based dip is shown, the dip consisting of eight ounces of heat treated whole green banana puree and ¼ cup of milk. In comparison, FIG. 4b shows a cream cheese based dip consisting of eight ounces of heat treated whole green banana puree and ¼ cup of milk. Both the green banana puree based dip and the cream cheese based dip remained homogeneous upon standing, without visible phase separation of water from the dip solids. As shown in the data in Table 3 below, the heat treated whole green banana puree based dip had very similar springiness and cohesiveness as the cream cheese based dip, but much greater force, hardness and chewiness. The consistency of the dip may be optimized as desired by adjusting the amount of banana puree included in the dip.

Figure 4C:
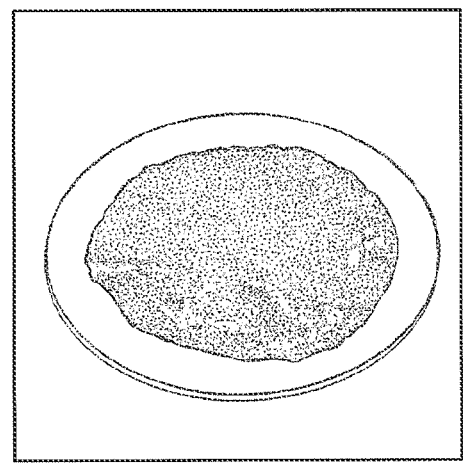
FIG. 4c shows a heat treated green banana based dip with oil and lemon juice.
Figure 4D:
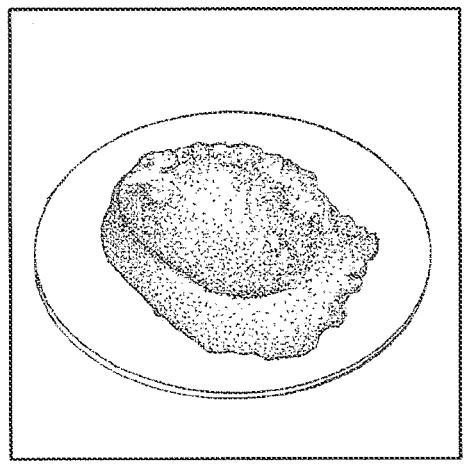
FIG. 4d shows a control dip containing chickpea paste, oil and lemon juice.

Referring to FIG. 4c, a green banana puree based dip is shown, the dip consisting of sixteen ounces of heat treated whole green banana puree, ¼ cup of oil and three tablespoons of lemon juice. In comparison, FIG. 4d shows a chickpea paste based dip consisting of sixteen ounces of chickpea paste ¼ cup of oil and three tablespoons of lemon juice. Both the green banana puree based dip and the chickpea based dip remained homogeneous upon standing, without visible phase separation of water from the dip solids. As shown in the data in Table 3 below, the heat treated whole green banana puree based dip had similar gumminess and chewiness as the chickpea paste based dip, but much greater force and hardness. Consequently, heat treated banana whole puree is suitable for use as a dip base, for example in place of such ingredients as cream cheese or chickpea paste.

TABLE 3

Texture profile analysis of dips containing heat treated whole green banana puree, cream cheese, or chickpea paste.

| Sample | Green Banana + Milk | Cream Cheese + Milk | Green Banana + Oil + Lemon | Chickpea Paste + Oil + Lemon |
|---|---|---|---|---|
| Force (g) | 714.8 ± 147.8 | 190.9 ± 7.23 | 432.6 ± 60.54 | 296.9 ± 22.5 |
| Hardness (g) | 784.4 ± 174.4 | 201.5 ± 8.4 | 512.0 ± 69.0 | 297.6 ± 30.7 |
| Adhesiveness (g · sec) | −694.8 ± 162.0 | −144.42 ± 11.17 | −14.4 ± 17.5 | −144.6 ± 15.6 |
| Springiness | 0.97 ± 0.01 | 0.96 ± 0.02 | 0.72 ± 0.21 | 0.98 ± 0.01 |
| Cohesiveness | 0.758 ± 0.06 | 0.781 ± 0.07 | 0.529 ± 0.06 | 0.818 ± 0.05 |
| Gumminess | 587.2 ± 78.2 | 157.33 ± 16.2 | 271.3 ± 52.0 | 243.1 ± 26.2 |
| Chewiness | 570.6 ± 80.9 | 150.73 ± 18.1 | 197.6 ± 79.4 | 239.0 ± 27.6 |
| Resilience | 0.029 ± 0.01 | 0.044 ± 0.004 | 0.23 ± 0.02 | 0.039 ± 0.01 |

Figure 5A:
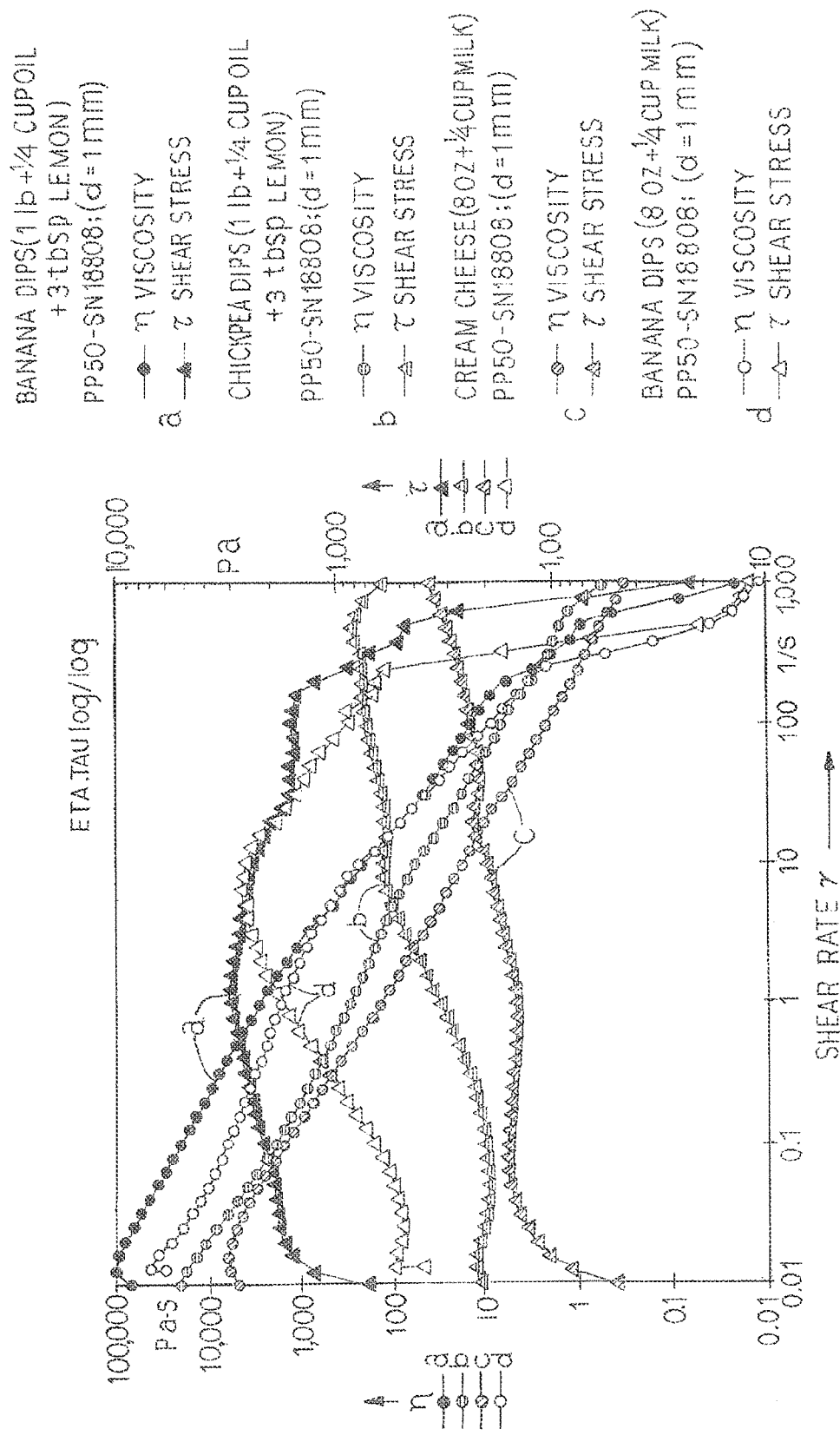
FIG. 5a provides a graph of rheology tests of dips, using the flow mode of a rheometer.
Figure 5B:
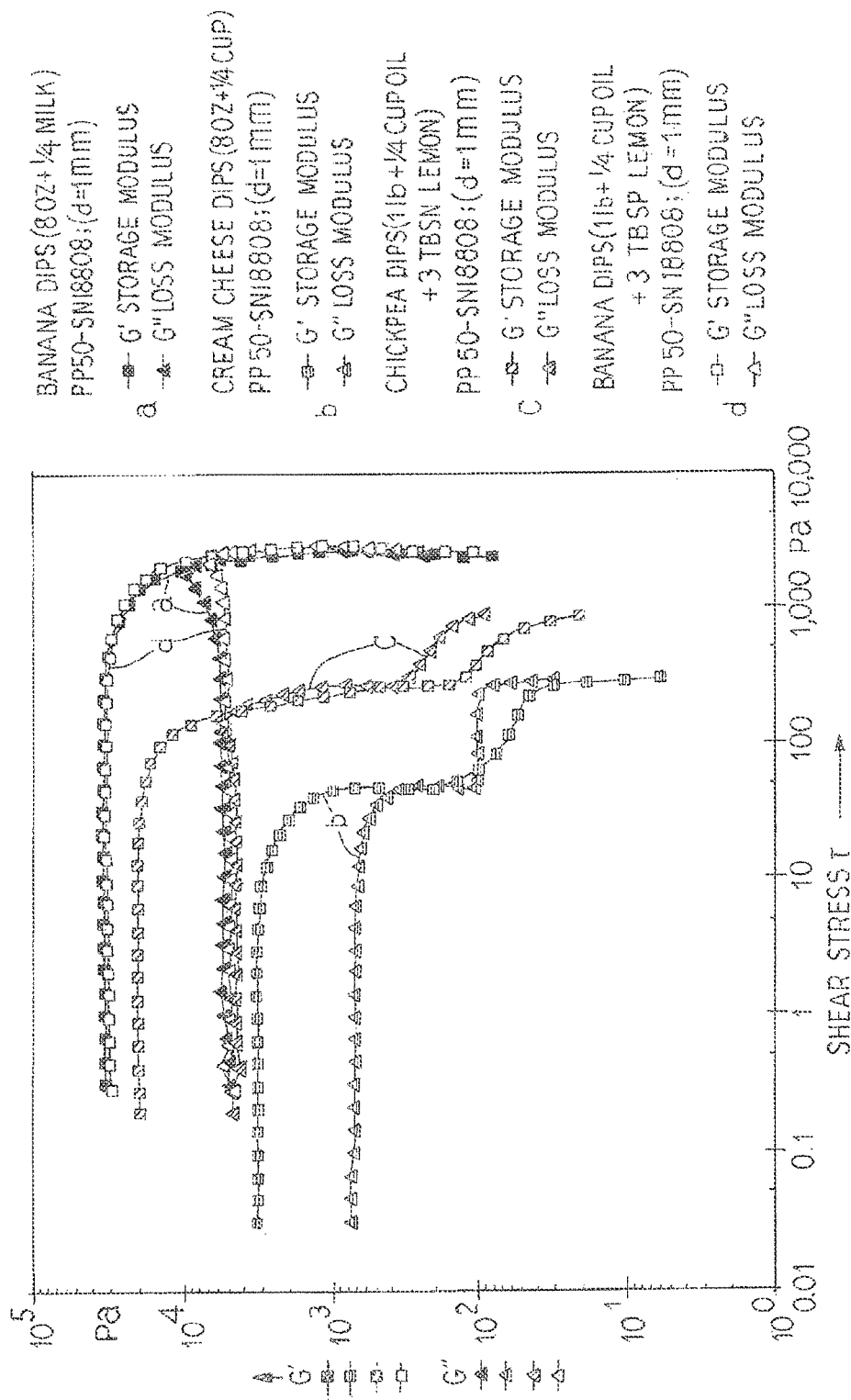
FIG. 5b provides a graph of rheology tests of dips, using the oscillatory mode of a rheometer.

The rheology of the four dips was tested, both with the flow mode and the oscillatory mode of a rheometer. Referring to FIG. 5a, flow mode rheology results are provided, as tested according to ASTM WK31279, with a gap distance of 1 millimeter, a 2° conical spindle, and temperature of 22° C., over a strain of 0-1000 sec$^{-1}$. As shown in FIG. 5a, the viscosity of the heat treated whole green banana puree based dips in the flow mode was higher than the viscosity of either the cream cheese based dip or the chickpea paste based dip. Similarly, referring to FIG. 5b, the oscillatory mode results are provided, as tested according to ASTM E2254-09 under the conditions noted above in Example 2. As shown in FIG. 5b, the storage modulus of the heat treated whole green banana puree based dip in the oscillatory mode of the rheometer was higher than the storage modulus of either the cream cheese based dip or the chickpea paste based dip.

Example 6

Figure 6:
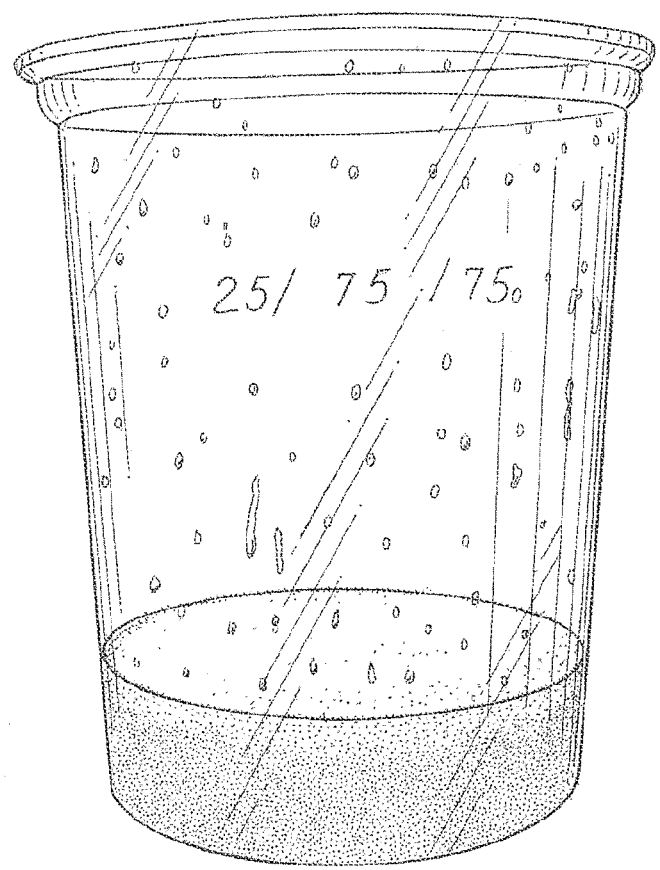
FIG. 6 shows a salad dressing containing heat treated whole green banana puree.

Heat treated whole green banana puree prepared according to Example 1 was tested for its capacity to act as a dressing/sauce base, such as a salad dressing. Typically, a dressing or sauce can be considered a diluted form of a dip, which should flow easily. Referring to FIG. 6, a heat treated whole green banana puree based dressing is shown, consisting of 75 grams balsamic vinegar and 75 grams olive oil mixed with 25 grams wet heat treated whole green banana puree. As shown in FIG. 6, no phase separation of oil and vinegar was observed; therefore the banana puree functioned as a dispersing ingredient. This result verified that heat treated whole green banana puree can successfully be employed as a dispensing/stabilizing/emulsifying agent in dilute solutions.

Example 7

Celiac disease is caused by the intolerance of gluten proteins of grains such as wheat, rye and barley. Heat treated whole green banana puree is an option for a substitution of the wheat flour to eliminate glutens from formulations. Accordingly, heat treated whole green banana puree prepared according to Example 1 was tested for its capacity to act as a gluten substitute, such as in baked products. Crackers were therefore prepared including heat treated whole green banana puree as a substitute for wheat flour, to eliminate glutens from the formulation. The formulations for banana puree/oat flour crackers and control wheat flour crackers are shown below in Table 4.

Figure 7A:
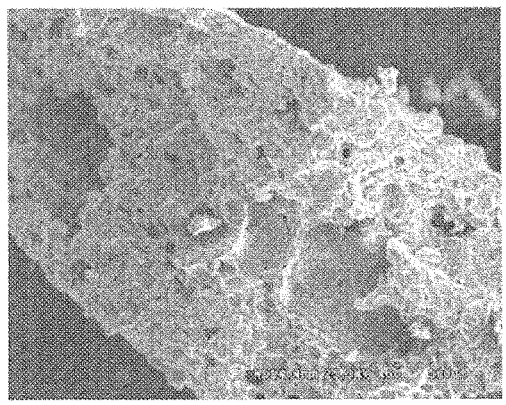
FIG. 7a shows the microstructure of a wheat based cracker.
Figure 7B:
FIG. 7b shows the microstructure of a banana and oat based cracker.

Referring to FIG. 7, micrographs having a magnification of 500× show that the banana puree and oat flour based crackers (FIG. 7b) exhibited a typical cracker foam structure, as compared to those of the control wheat flour crackers (FIG. 7a).

TABLE 4

Cracker formulations.

| Ingredient | Banana Puree Cracker | Wheat Flour Cracker |
|---|---|---|
| Heat Treated Whole Green Banana Powder | 36% | |
| Whole Oat Flour | 36% | |
| Whole Wheat Flour | | 72% |
| Starch | 10% | 10% |
| Waxy Starch | 10% | 10% |
| Sugar | 6% | 6% |

TABLE 4-continued

Cracker formulations.

| Ingredient | Banana Puree Cracker | Wheat Flour Cracker |
|---|---|---|
| Lecithin Powder | 1% | 1% |
| Baking Powder | 1% | 1% |
| Total: | 100% | 100% |

Figure 8A:
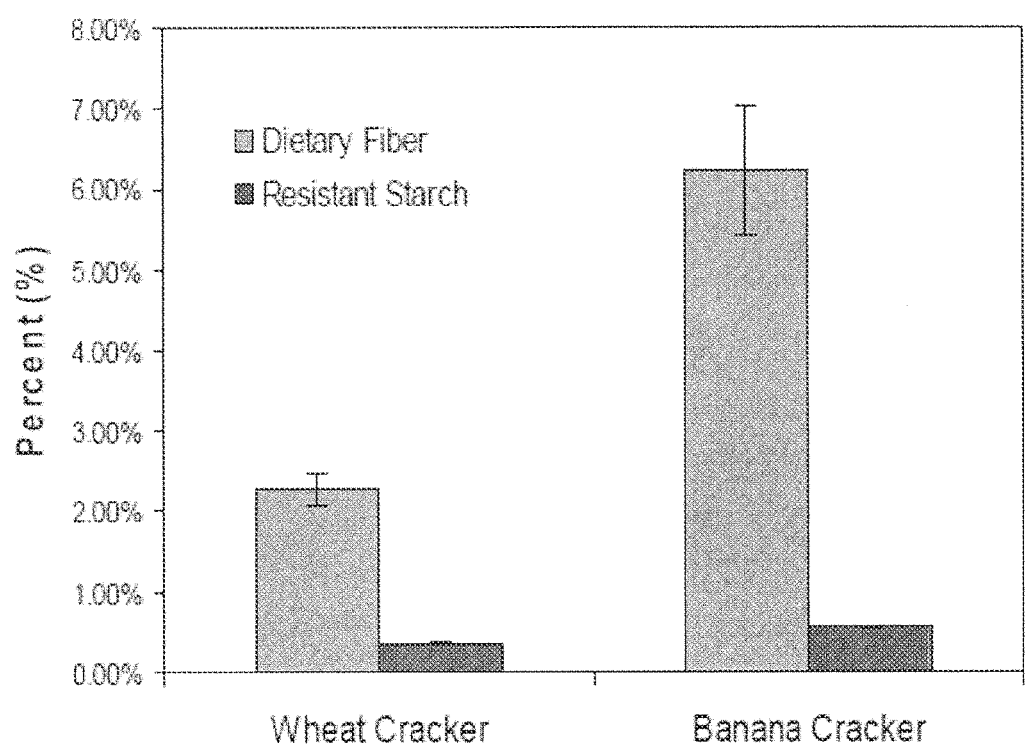
FIG. 8a provides a graph of the dietary fiber content of crackers.
Figure 8B:
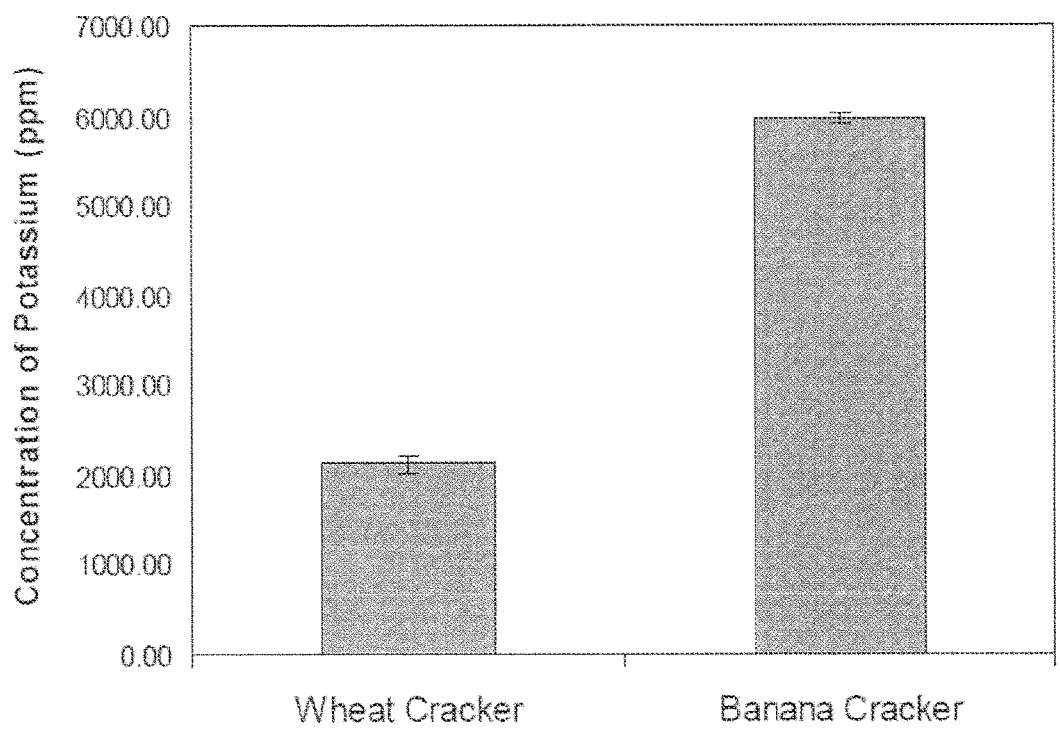
FIG. 8b provides a graph of the potassium content of crackers.
Figure 8C:
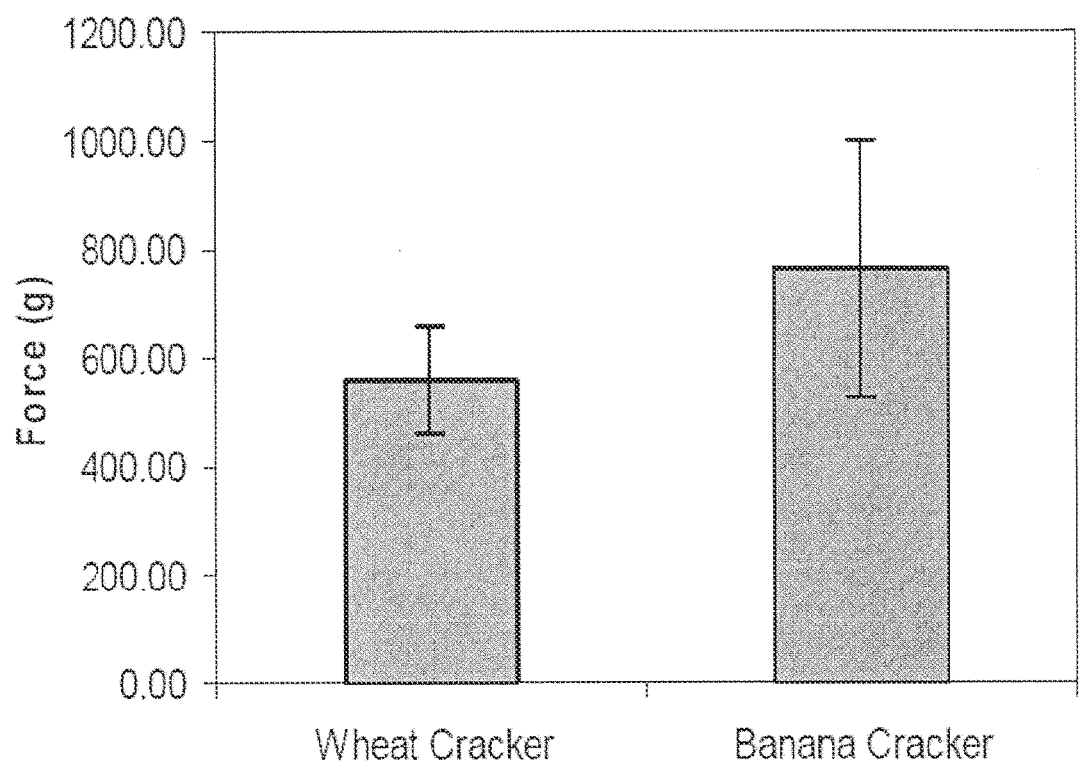
FIG. 8c provides a graph of the firmness of crackers.
Figure 9A:
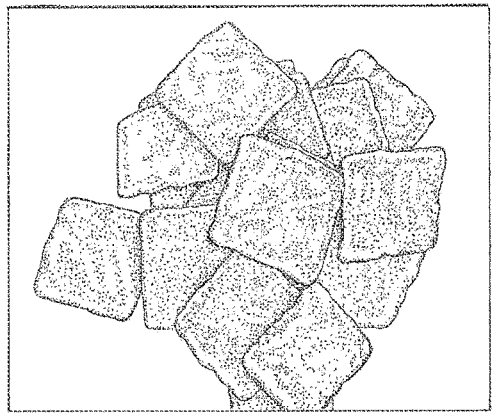
FIG. 9a shows gluten-free baked banana puree crisps.
Figure 9B:
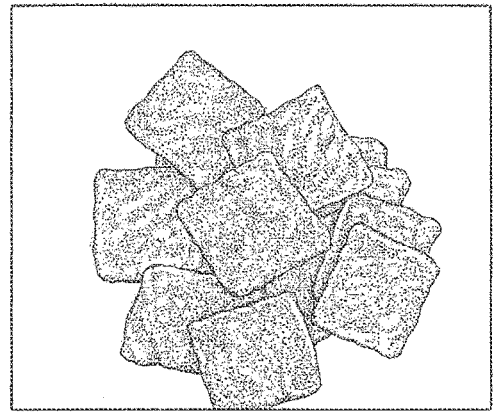
FIG. 9b shows gluten-free baked crackers containing banana puree and strawberry pomace.
Figure 9C:
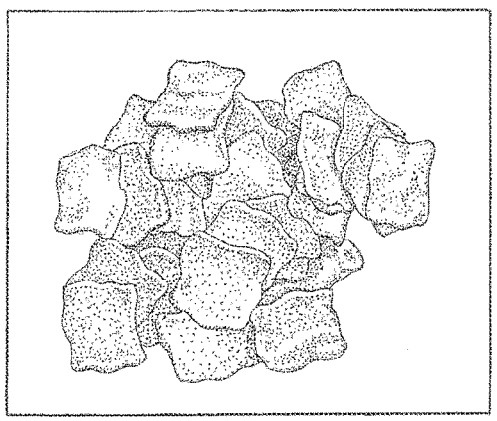
FIG. 9c shows gluten-free baked crackers containing banana puree.
Figure 9D:
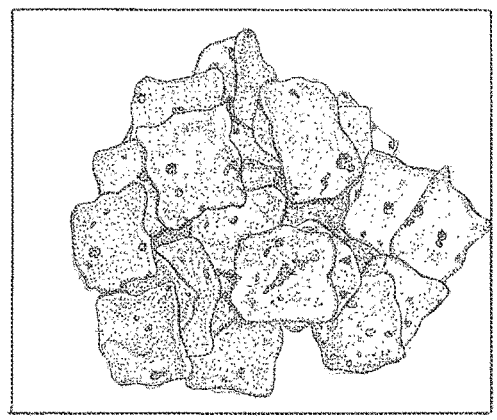
FIG. 9d shows gluten-free baked crackers containing banana puree, blueberries and cranberries.

Moreover, referring to FIG. 8, in addition to providing gluten replacement, the banana puree/oat flour crackers provided higher fiber (FIG. 8a) and potassium (FIG. 8b) contents as well as greater firmness (FIG. 8c) than provided by wheat based crackers. Physicochemical characteristics of the banana puree/oat flour crackers and wheat flour crackers were tested and are provided in Table 5 below. As demonstrated by the results in Table 5, the banana puree and oat flour based crackers exhibited similar physical properties compared to those of the control wheat flour crackers.

TABLE 5

Physicochemical characteristics of crackers

| Physicochemical Attribute | Banana Puree Cracker | Wheat Flour Cracker |
|---|---|---|
| Moisture content (wt. %) | 1.58 ± 0.12 | 2.43 ± 0.4 |
| Oil content (wt. %) | 12.22 ± 0.17 | 11.34 ± 0.14 |
| Bulk density (g/cc) | 1.41 ± 0.02 | 1.41 ± 0.08 |
| Surface area (mm$^2$) | 1241.21 ± 32.40 | 1218.55 ± 30.01 |
| Total sugar (wt. %) | 22.35 ± 0.32 | 11.01 ± 0.3 |
| Nitrogen (wt. %) | 0.84 ± 0.01 | 0.91 ± 0.02 |
| pH | 5.33 ± 0.02 | 6.26 ± 0.06 |
| Beta carotene (μg/100 g) | 50.00 ± 0.0 | 20.00 ± 0.0 |
| Vitamin A from carotene (IU/100 g) | 91.37 ± 4.4 | 35.00 ± 0.0 |
| Color L* | 48.08 ± 1.37 | 74.00 ± 0.62 |
| Color a* | 6.08 ± 0.37 | 1.61 ± 0.11 |
| Color b* | 18.22 ± 0.21 | 19.00 ± 1.12 |

Referring to FIG. 9, the gluten-free banana puree/oat flour crackers are also capable of holding various dried fruit pieces in the cracker, such as to add flavor enhancement. In particular, FIG. 9a shows banana puree crisp crackers, FIG. 9b shows banana puree and strawberry pomace crisp crackers, FIG. 9c shows banana puree crackers, and FIG. 9d shows banana puree, blueberry and cranberry crackers.

Example 8

Heat treated green banana puree powder was tested for its capacity to act as a natural binder. In contrast to the heat treated green banana puree of Example 1, the heat treated green banana was first pureed, then dried using drum drying and hot air drying, and then ground to form a powder by the powder manufacturer. The green banana powder, therefore, was heat treated during the drying processes. The dried powder of green banana puree was tested as a natural binder with grape juice concentrate.

Figure 10A:
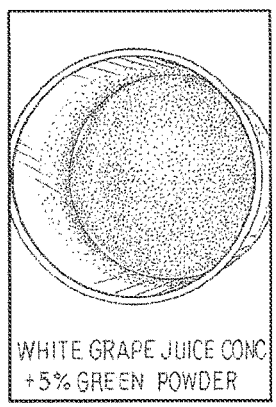
FIG. 10a shows a natural binder including 5% dried heat treated green banana puree and grape juice concentrate.
Figure 10B:
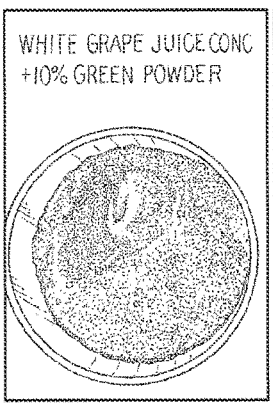
FIG. 10b shows a natural binder including 10% dried heat treated green banana puree and grape juice concentrate.
Figure 10C:
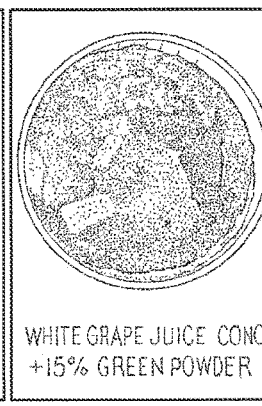
FIG. 10c shows a natural binder including 15% dried heat treated green banana puree and grape juice concentrate.
Figure 10D:
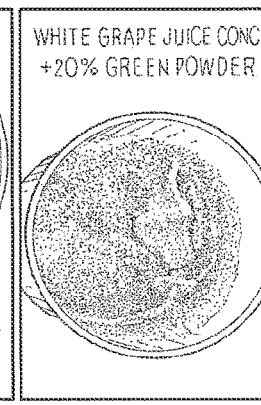
FIG. 10d shows a natural binder including 20% dried heat treated green banana puree and grape juice concentrate.
Figure 10E:
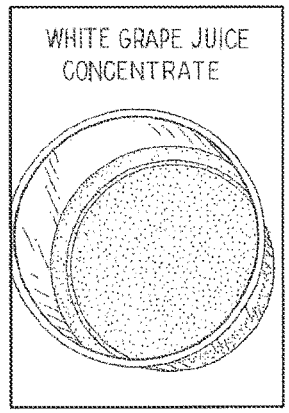
FIG. 10e shows a natural binder including grape juice concentrate.

The heat treatment gelatinized the green banana starches and increased the gelation property of the powder, and it was discovered that the green banana powder acts as an excellent cold-set gelation material after rehydration due to its pre-gelatinized structure. FIG. 10 shows the gelation phenomenon of green banana puree powder after blending with grape juice concentrate, which is a hydrating and sweetening agent. In particular, FIG. 10 shows compositions containing white grape juice concentrate (FIG. 10e), white grape juice concentrate with 5% by weight whole green banana powder (FIG. 10a), white grape juice concentrate with 10% by weight whole green banana powder (FIG. 10b), white grape juice concentrate with 15% by weight whole green banana powder (FIG. 10c), and white grape juice concentrate with 20% by weight whole green banana powder (FIG. 10d).

The addition of 5% by weight whole green banana powder to white grape juice concentrate added cloudiness to the juice and darkened the color of the juice. The addition of 10% by weight whole green banana powder to white grape juice concentrate resulted in partial gelation of the composition, with some remaining liquid separated from the gelled juice and whole green banana powder composition. The addition of 15% by weight whole green banana powder to white grape juice concentrate resulted in a substantially complete gelation of the composition, with no visible phase separation of juice from the whole green banana powder. The addition of 20% by weight whole green banana powder to white grape juice concentrate resulted in a complete gelation of the composition, and exhibiting a darker color than the compositions containing 0-15% by weight powder.

Figure 11:
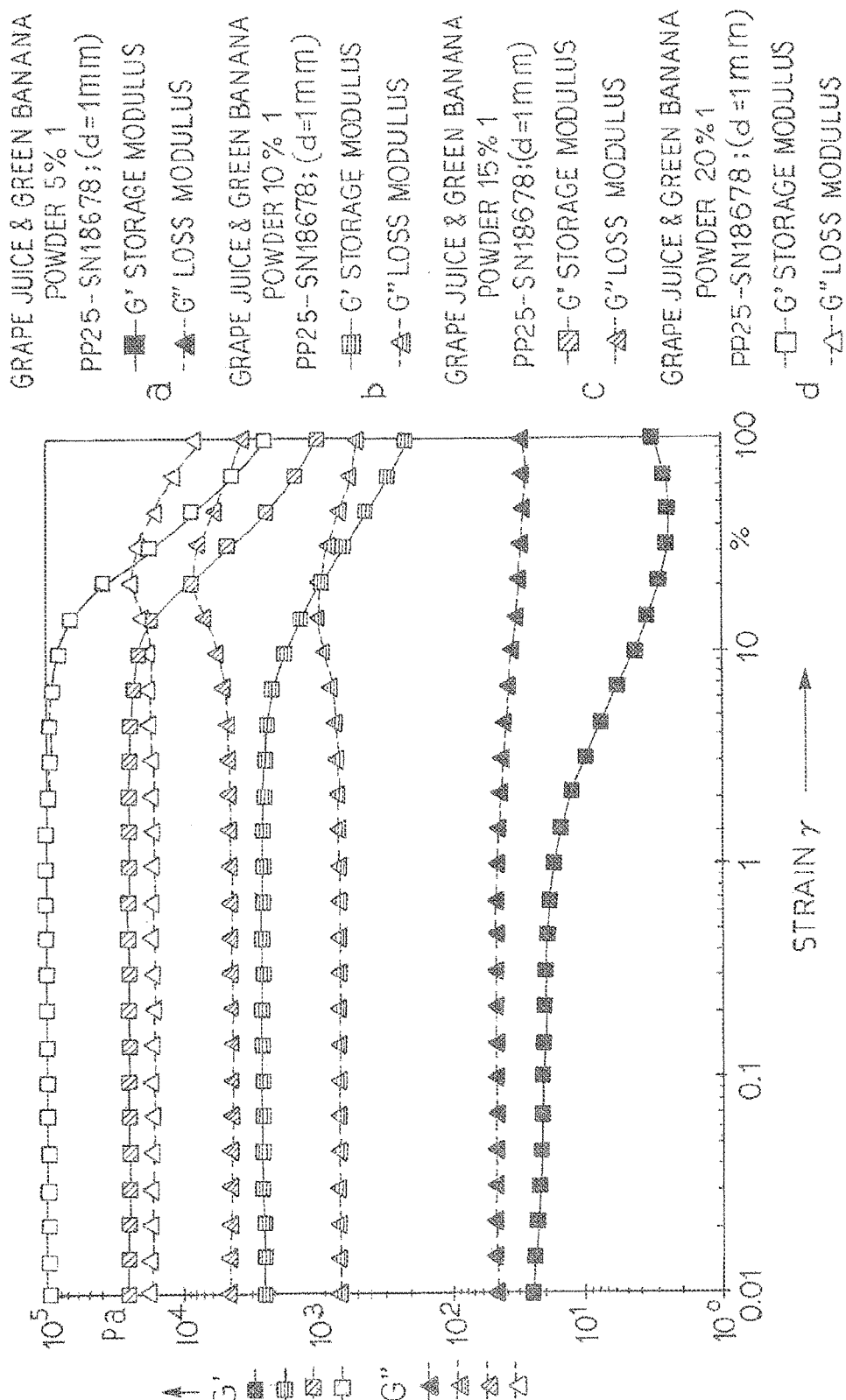
FIG. 11 provides a graph of the viscosities of the natural binders of FIG. 10.

The viscosities of the compositions shown in FIG. 10 were measured according to ASTM E2254-09 described above, and the viscosity results demonstrated that the higher the percentage of whole green banana powder, the higher the viscosity of the composition. Referring to FIG. 11, a graph of the viscosity data is provided.

Figure 12A:
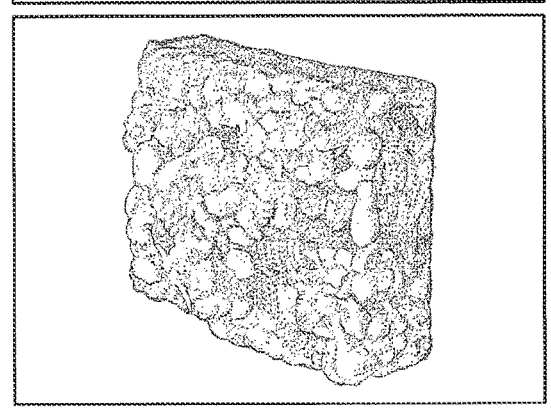
FIG. 12a shows a chewy granola bar with a control binder containing sugar.
Figure 12B:
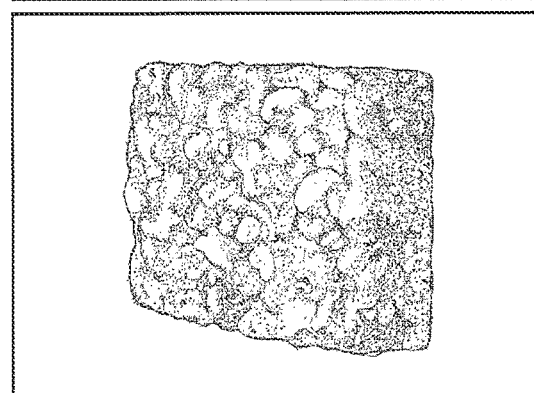
FIG. 12b shows a chewy granola bar with a green banana, grape juice concentrate, and glycerol based binder.
Figure 12C:
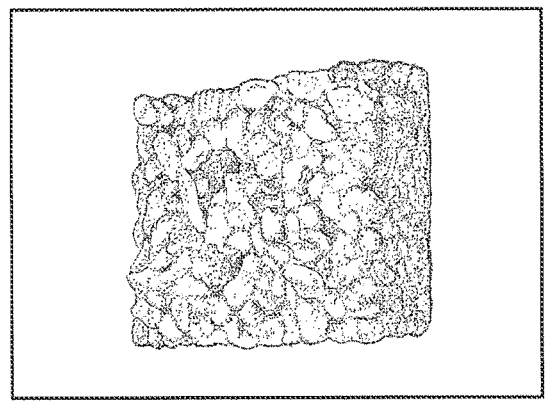
FIG. 12c shows a chewy granola bar with a green banana and grape juice concentrate based binder.
Figure 12D:
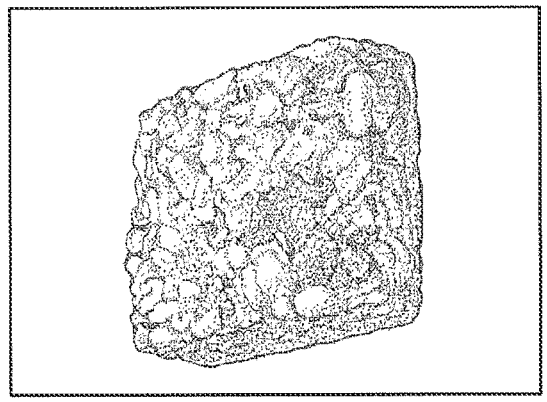
FIG. 12d shows a chewy granola bar with a green banana and grape juice concentrate based binder.

The whole green banana powder in white grape juice concentrate was then employed as a natural binder for granola bars. Referring to FIG. 12, chewy granola bars are shown comprising green banana puree based binders. FIG. 12a shows a control granola bar in which the bar is composed of 65% by weight grains and 35% by weight binder, wherein the binder comprises a commercial sugar binder. FIG. 12b shows a granola bar in which the bar is composed of 80% grains and 20% binder, wherein the binder comprises 10% by weight whole green banana powder, 78% by weight white grape juice concentrate, and 12% by weight glycerol. FIG. 12c shows a granola bar in which the bar is composed of 80% grains and 20% binder, wherein the binder comprises 10% by weight whole green banana powder and 90% by weight white grape juice concentrate. FIG. 12d shows a granola bar in which the bar is composed of 90% grains and 10% binder, wherein the binder comprises 10% by weight whole green banana powder and 90% by weight white grape juice concentrate. The binders comprising whole green banana powder were effective as binders for granola bars.

In addition to the benefits of providing a binding capacity, the use of green banana puree powder also allows for the possibility of preparing "whole" and "natural" products, which is in contrast to current commercial binders that contain various artificial ingredients, for instance preservatives and surfactants.

Example 9

Figure 13A:
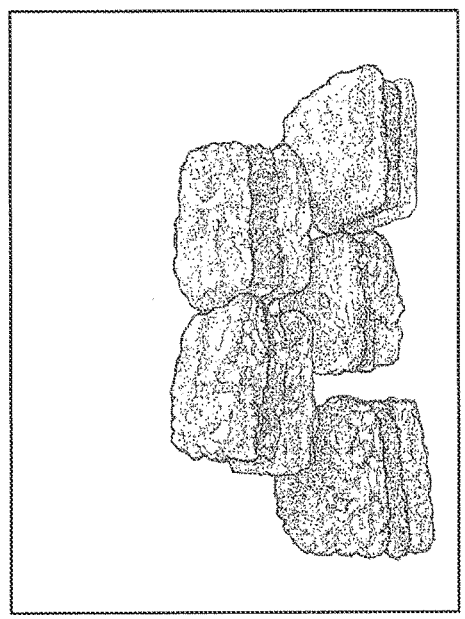
FIG. 13a shows oatmeal fruit cookie sandwiches having a filling containing heat treated green banana powder.
Figure 13B:
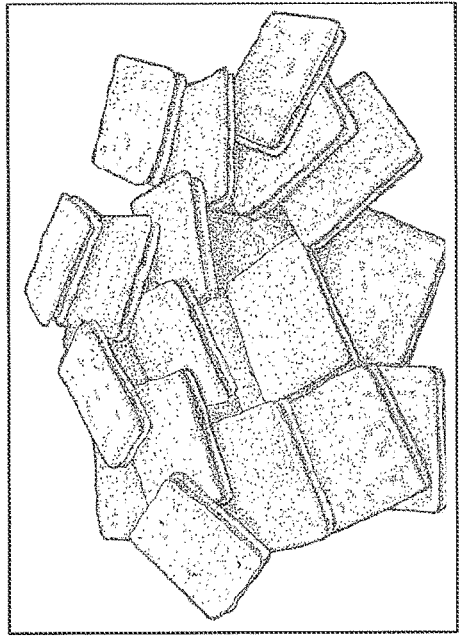
FIG. 13b shows fruit cracker sandwiches having a filling containing heat treated green banana powder.
Figure 13C:
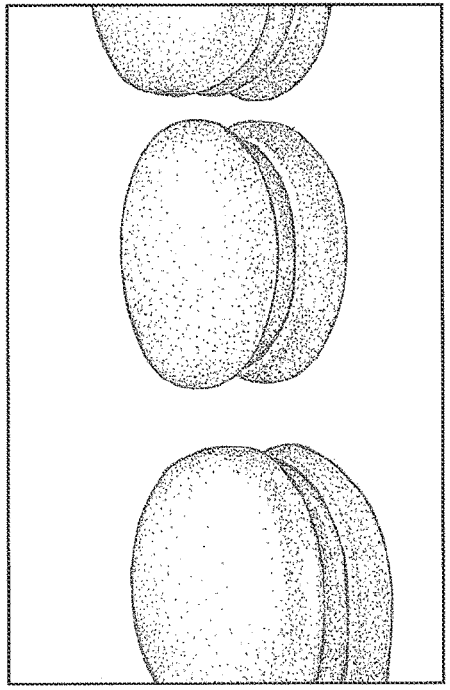
FIG. 13c shows shortcake fruit sandwiches having a filling containing heat treated green banana powder.
Figure 13D:
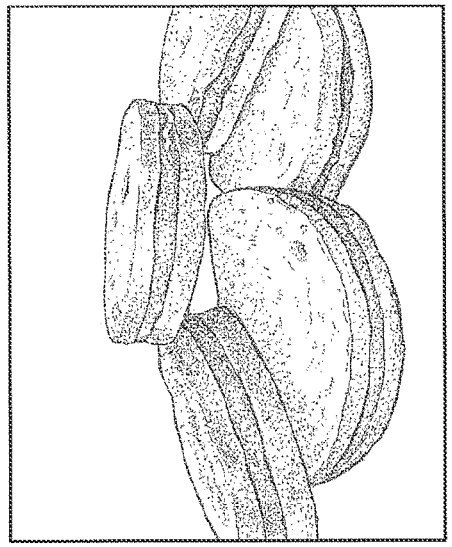
FIG. 13d shows peanut butter bagel sandwiches having a filling containing heat treated green banana powder.

Mini-meals and snacks were prepared according to certain embodiments of the invention. A mixture of 15 grams green banana powder, 5 grams dehydrated fruit solids and 90 grams fruit juice concentrate was heated with occasional stirring in a water bath for 30 minutes to form a gel with a water activity below 0.5. The resulting gels were spread on cookies, crackers, shortcakes, and bagels, and baked for 7 minutes at 300 degrees Fahrenheit in a forced convection oven to make approximately 300 grams of corresponding sandwich products. Referring to FIG. 13a, oatmeal fruit cookie sandwiches are shown having a filling containing green banana powder. Referring to FIG. 13b, fruit cracker sandwiches are shown having a filling containing green banana powder. Referring to FIG. 13c, shortcake fruit sandwiches are shown having a filling containing green banana powder. Referring to FIG. 13d, peanut butter bagel sandwiches are shown having a filling containing green banana powder. Moreover, for peanut butter jelly sandwich snacks, peanut butter chips or peanut flour was added to the gel before spreading the filling on bagel toast. The fillings comprising whole green banana powder were effective to secure the two halves of the sandwiches together for each of the products prepared according to Example 9.

Example 10

Figure 14:
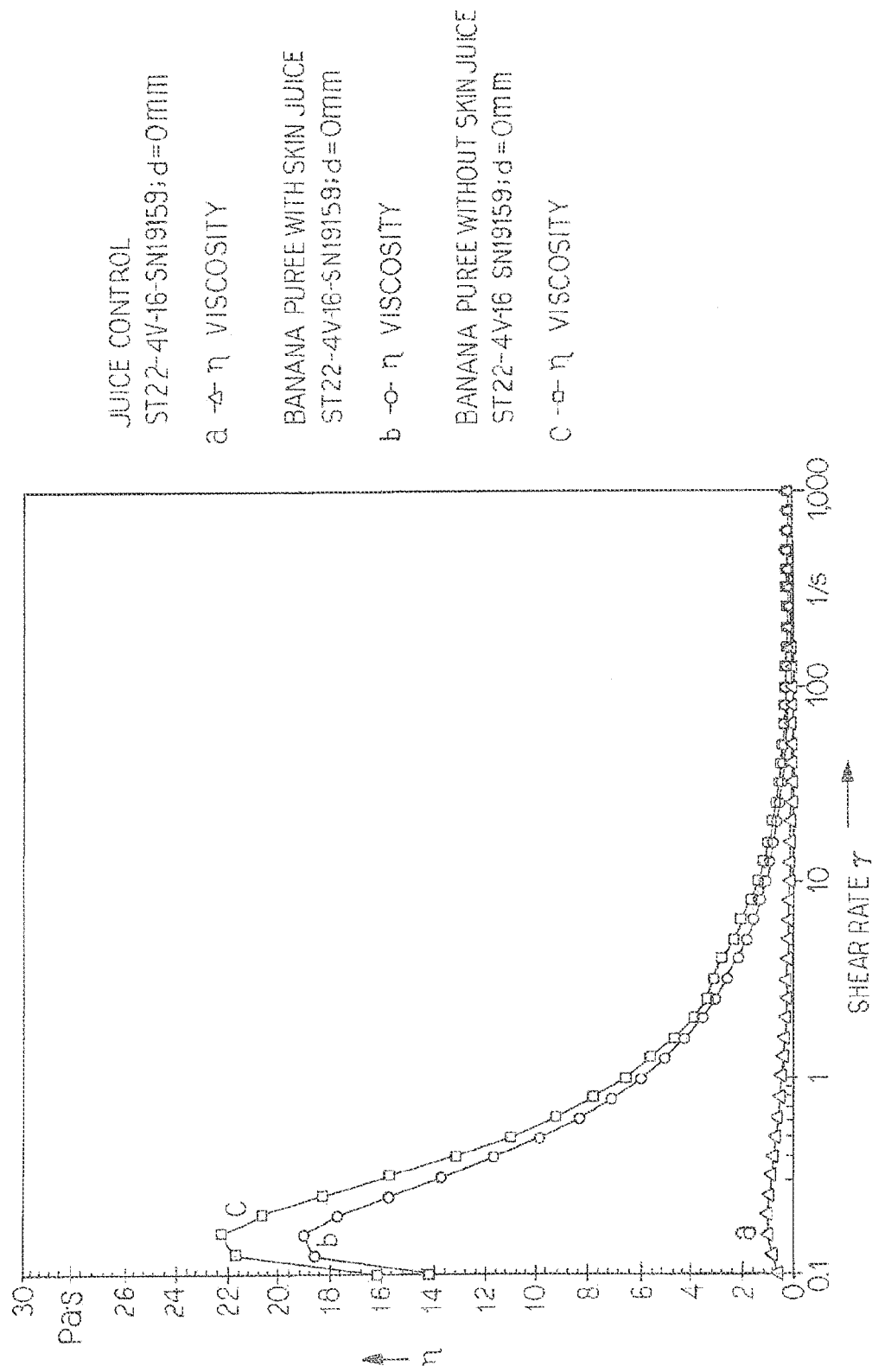
FIG. 14 provides a graph of the viscosities of compositions containing heat treated green banana pulp puree or whole green banana puree.

The viscosity of compositions containing heat treated green banana puree (prepared according to the method of Example 1) was tested using a rapid visco analyzer, and the measured viscosities are shown in FIG. 14. The experimental conditions follow Newport Scientific Method ST-00 (General method for testing starch in the Rapid Visco Analyzer). Total sample amounts in the test can were 28 grams, including water and a dry powder of the puree. The viscosity values demonstrate that the heat treatment increases the viscosity of the green banana puree, as does the inclusion of banana peel.

Referring to FIG. 15a, a beverage composition is shown comprising fruit puree, oat flour and fruit solids, which served as the control sample for the viscosity measurements. The control sample exhibited phase separation upon standing for at least 30 minutes, in which about forty percent by volume of the beverage composition was present as a water phase on top of the phase containing the majority of the solids. Referring to FIG. 15b, a composition is shown comprising 5 weight percent green banana pulp puree and 95 weight percent of the control beverage containing fruit puree, oat flour and fruit solids. In contrast to the control composition, the beverage composition containing 5 weight percent green banana pulp puree exhibited phase separation upon standing for at least 30 minutes, in which about twenty percent by volume of the beverage composition was present as a water phase. Referring to FIG. 15c, a composition is shown comprising 5 weight percent whole green banana puree and 95 weight percent of the control beverage containing fruit puree, oat flour and fruit solids. The beverage composition containing 5 weight percent whole green banana puree exhibited little phase separation upon standing for at least 30 minutes, in which between only about five to ten percent by volume of the beverage composition was present as a water phase. Consequently, heat treated green banana pulp puree is significantly effective for suspending particles even at an amount of only 5 weight percent in a beverage composition. Heat treated whole green banana puree is at least twice as effective for suspending particles at an amount of 5 weight percent in a beverage composition as heat treated green bananas without the peel.

Referring back to FIG. 14, the viscosity of the beverage is shown to increase considerably as a result of addition of banana to the beverage, i.e., from about 1 cP to about 19 cP (for the beverage containing whole banana puree) or to about 22 cP (for the beverage containing banana pulp puree). The difference between the measured viscosities of 19 cP and 22 cP was not statistically significant.

The addition of banana puree also increased particulate suspension shelf life. For example, retention factor (Rf) values of the three samples indicate that particulate height retention in the beverage after 6 weeks of refrigerated storage was 0.4 for the control beverage with no added banana puree. In contrast to the control, the beverage containing added green banana puree had a lower Rf value, of 0.15, and the beverage containing the whole banana puree had an Rf value of just 0.05. Rf values are unitless and commonly used in chromatography, particularly thin layer chromatography. As used herein, Rf values represent the distance traveled down by the particulates relative to the original particulate length. Stated another way, the Rf values represent the height of the clear liquid phase relative to the initial suspended juice height, thus the Rf measurement corrects for differences in the original lengths of particulates of multiple samples. Consequently, the addition of green banana puree resulted in greater particulate suspension over time than exhibited in the control beverage, while the addition of whole banana puree resulted in greater particulate suspension over time than exhibited in the beverage containing green banana puree.

Example 11

Referring to FIGS. 16 and 17, exemplary food products are shown in which banana purees or powders according to embodiments of the invention may be employed. These products include, for example and without limitation, fruit dips, spreads, spoonable desserts and toppings containing over 95% fruit with no added gums, colloids, or gelatinized starches. Other ingredients added (oats, fiber, protein) were not added for functionality but rather to incorporate desirable nutrients in the product. Desired textures were accomplished with addition of banana ingredients. This includes the ability to develop whipped 100% fruit with no added dairy or legume, and to layering of multiple fruit without the need to incorporate pretreated/pre-gelatinized starch.

Figure 17A:
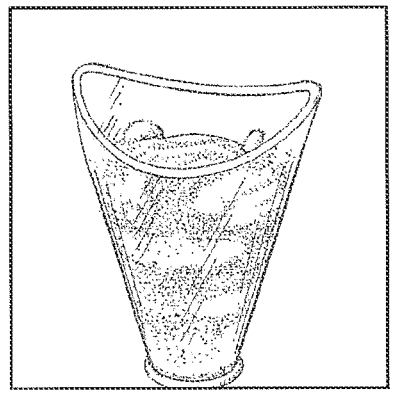
FIG. 17a shows a peaches and cream layered dessert containing a combination of heat treated whole green banana powder and heat treated green banana puree.
Figure 17B:
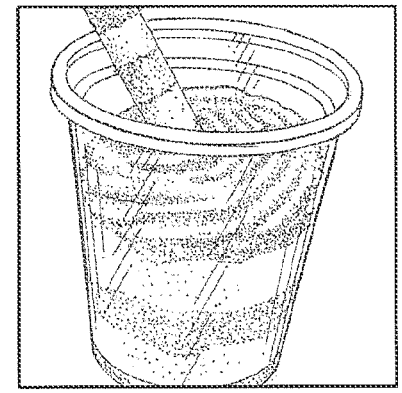
FIG. 17b shows a banana chocolate mousse layered dessert containing a combination of heat treated whole green banana powder and heat treated green banana puree.
Figure 17C:
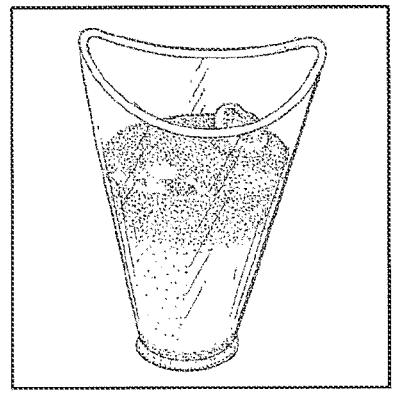
FIG. 17c shows a lemon berry layered dessert containing a combination of heat treated whole green banana powder and heat treated green banana puree.
Figure 17D:
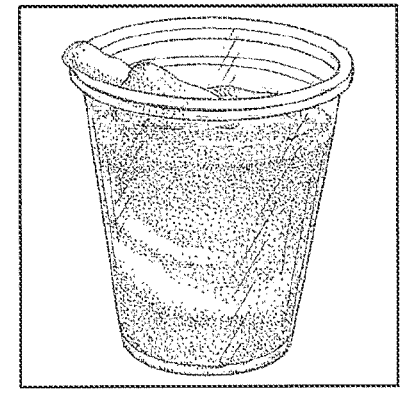
FIG. 17d shows a red berry layered dessert containing a combination of heat treated whole green banana powder and heat treated green banana puree.
Figure 17E:
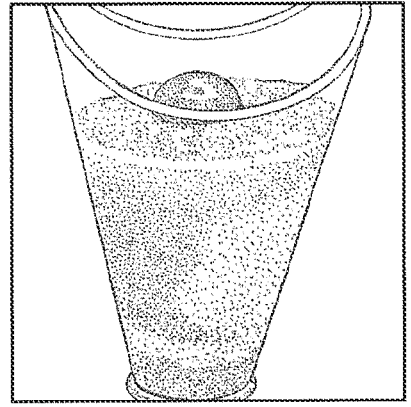
FIG. 17e shows a pineapple upside down cake layered dessert containing a combination of heat treated whole green banana powder and heat treated green banana puree.

For example, FIG. 16 shows various dips, such as berry dip (FIG. 16a), marinara pizza dip (FIG. 16b), or pineapple banana dip (FIG. 16c). Each dip comprising heat treated green banana remains homogeneous. FIG. 17 shows exemplary layered desserts comprising a combination of whole green banana puree and green banana powder, including peaches and cream (FIG. 17a), banana chocolate mousse (FIG. 17b), lemon berry (FIG. 17c), red berry (FIG. 17d), and pineapple upside down cake (FIG. 17e). The layered desserts comprising heat treated green banana puree maintain their phase separation, including separation of color between the various layers. Advantages of such fruit desserts include, for instance, the option of preparing desserts having up to 100% fruit content without added sugar, flavors, gum, or other additives. Moreover, the fruit desserts provide nutrition and encourage consumption of ingredients such as fiber, oats, and other whole grains. Fruit desserts comprising the heat treated banana products of embodiments of the invention further provide different alternatives to other dessert products, and are optionally shelf stable.

Example 12

Figure 18A:
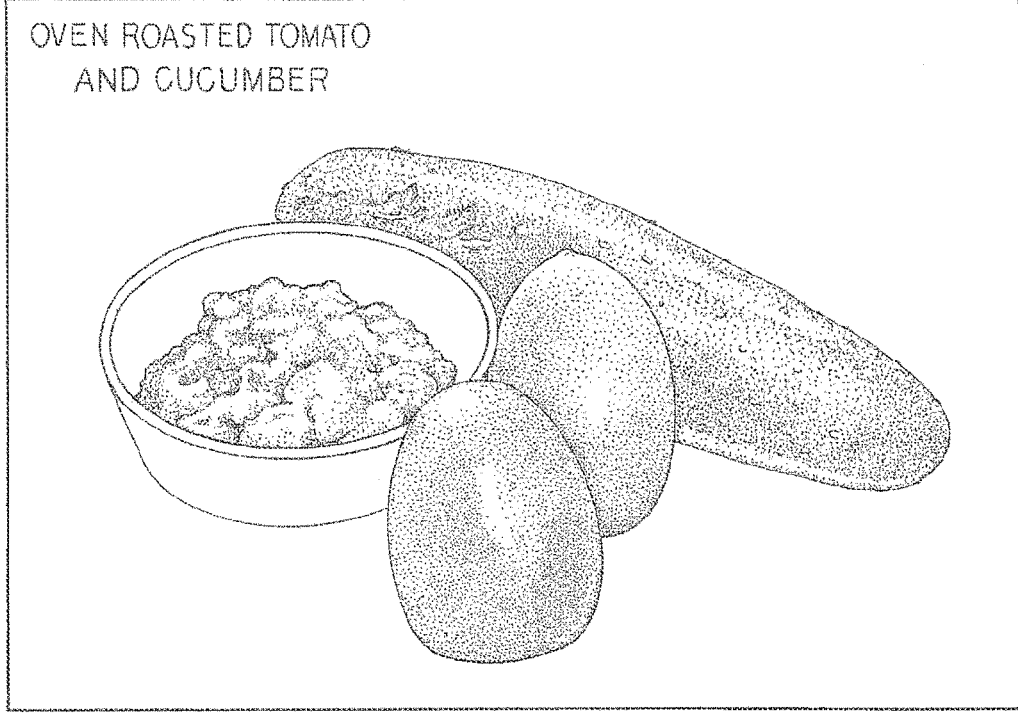
FIG. 18a shows a vegetable and fruit dip containing heat treated whole green banana powder.

Referring to FIGS. 18 and 19, exemplary dips are shown in which heat treated green banana puree or powder according to embodiments of the invention may be employed. FIG. 18a shows an exemplary vegetable and fruit dip comprising whole green banana powder prepared according to an embodiment of the present invention. In particular, FIG. 18a shows an oven roasted tomato cucumber dip having the ingredients listed below in Table 6. The dip comprising heat treated whole green banana powder maintains its homogeneity upon standing. A 31 gram serving of the tomato cucumber dip provides 30 calories, with 0 grams of fat, 1 gram of fiber, 4 grams of sugar, and 1 gram of protein. The full Nutrition Facts for the tomato cucumber dip are shown in FIG. 18b.

TABLE 6

Figure 19A:
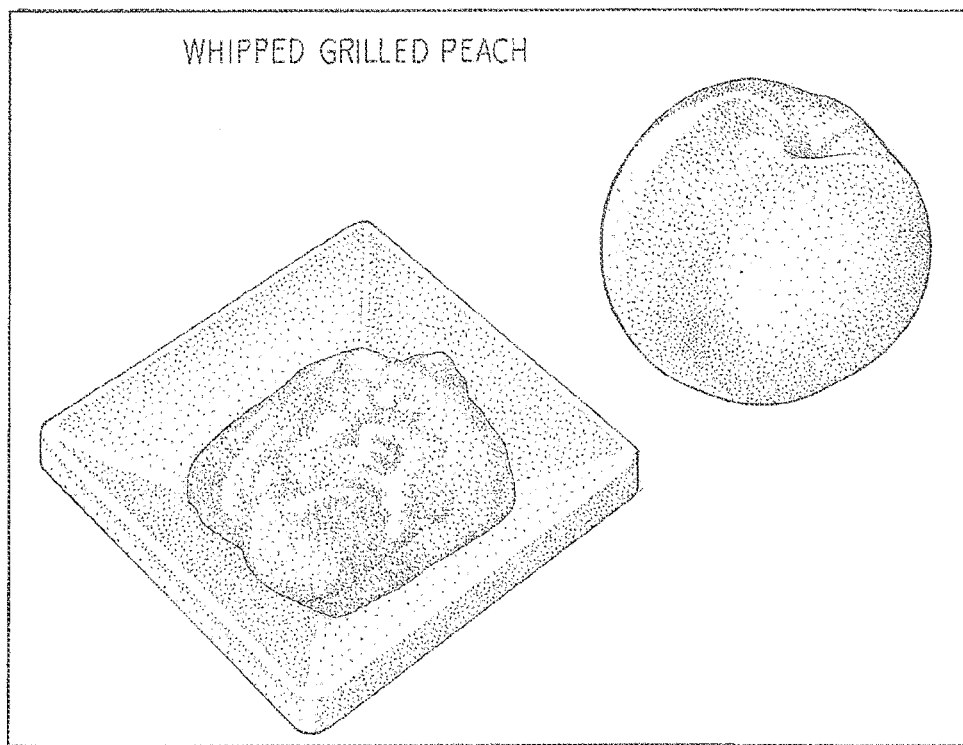
FIG. 19a shows a fruit dip containing heat treated whole green banana powder.

Ingredient list for oven roasted tomato cucumber dip.
Oven Roasted Tomato Cucumber Dip Honeydew Melon Juice
Banana Powder
Lemon Juice
Honeydew Melon Pulp
Cucumber Pulp
Oven Dried Tomatoes in Oil
Fresh Garlic
Fresh Parsley
Salt
Pepper FIG. 19a shows an exemplary fruit dip comprising whole green banana powder prepared according to an embodiment of the present invention. In particular, FIG. 19a shows a whipped grilled peach dip having the ingredients listed below in Table 7. The dip comprising heat treated whole green banana powder maintains its homogeneity upon standing. A 31 gram serving of the peach dip provides 25 calories, with 0 grams of fat, 0 grams of fiber, 2 grams of sugar, and 0 grams of protein. The full Nutrition Facts for the tomato cucumber dip are shown in FIG. 19b.

TABLE 7

Ingredient list for whipped grilled peach dip
Whipped Grilled Peach Dip

Fresh Yellow Peaches
Apple Juice Concentrate
Vanilla Bean Extract
Lemon Juice
White Peach Puree
Water
Banana Powder Example 13

Whole green banana powder in white grape juice concentrate was tested as a natural binder for granola bars. In a first embodiment the natural binder comprised 20 wt. % green banana powder, 12 wt. % glycerol, and 68 wt. % grape juice concentrate. In a second embodiment, the natural binder comprised 10 wt. % green banana powder, 12 wt. % glycerol, and 78 wt. % grape juice concentrate. The solids of the granola bars comprised 72 wt. % granola, 17 wt. % brown rice crisps, and 11 wt. % chocolate chips. The granola bars each comprised 64 wt. % grains/solids and 36 wt. % binder. The granola bars did not contain any added salt.

The finished granola bars exhibited neutral flavor without any detectable banana flavor provided by the binder. The granola bars having a binder comprising 20 wt. % green banana powder exhibited a hard texture, while the granola bars having a binder comprising 10 wt. % green banana powder exhibited a chewy texture. Accordingly, the texture of a granola bar can be tuned by selecting the amount of green banana powder included in the bar binder. As demonstrated, a binder comprising 20% green banana powder is suitable for a hard or crunchy granola bar. In contrast, a binder comprising 10% or less green banana powder binder is suitable for a chewy granola bar. The binders comprising whole green banana powder were thus effective as binders for granola bars.

In addition to the benefits of providing a binding capacity, the use of green banana puree powder also allows for the possibility of preparing "whole" and "natural" products, which is in contrast to current commercial binders that contain various artificial ingredients, for instance preservatives and surfactants.

Example 14

Whole green banana powder in white grape juice concentrate was employed as a natural binder for granola bars. The finished product comprised the formulation provided below in Table 8, and the nutrition facts are provided in Table 9 below. Each 37 gram bar contained three quarters of a serving of whole grains, half of a serving of fruit/fruit juice, as established by the USDA. The natural binder was 36 wt. % of the total snack bar, while the particulate ingredients combined were 64 wt. % of the total snack bar.

TABLE 8

Granola bar formulation containing whole grain, fruit and nuts.

| Ingredient | Weight percent |
|---|---|
| Particulates | |
| Oats | 25% |
| Wheat | 9% |
| Blueberries | 15% |
| Almonds | 15% |
| Binder Syrup | |
| Grape Juice Concentrate | 23% |
| Heat Treated Green Banana Powder | 8% |
| Glycerin | 4.5% |
| Sea Salt | 0.5% |
| Total: | 100% |

TABLE 9

Nutrition facts for granola bar containing whole grain, fruit and nuts.

| Nutrition Facts | Per 37 gram Bar |
|---|---|
| Calories | 130 |
| Calories from fat | 35 |
| Total fat (g) | 3.5 |
| Saturated fat (g) | 0.5 |
| Sodium (mg) | 70 |
| Total carbohydrates (g) | 25 |
| Dietary fiber (g) | 2.5 |
| Sugars (g) | 11 |
| Protein (g) | 3 |

Example 15

A binder for granola bars was tested, in which a mixture of whole green banana powder in white grape juice concentrate was employed as a natural binder for the granola bars. The natural binder was mixed with the solid, particulate bar ingredients until the particulates were coated with the binder. The natural binder was 36 wt. % of the total granola bar, while the particulate ingredients combined were 64 wt. % of the total granola bar. The coated particulates were then compressed together and cooled to form the finished granola bar. Accordingly, the binder is required to exhibit both liquid and solid properties: liquid properties to effectively coat the particulates, followed by solid properties upon cooling to effectively bind the particulates together in the granola bar. The binder comprising whole green banana powder was thus successful as a binder for granola bars.

Example 16

Green banana powder was used as a binding agent and bulking material to reduce or replace sugar in high sugar products such as binder syrups, which are commonly used in granola bars, and cookies. Green banana powder was tested in binder syrup by replacing sugar, as shown in Table 10 below. Formula 3 resulted in a binder syrup that most closely resembled the control. The inventors believe that Formulas 1 and 2 resulted in a higher complex viscosity than Formula 3 and the control because green banana powder binds more water and thus increases the viscosity due to the starch content.

TABLE 10

Binder syrup formulations

| Ingredients | Control (wt %) | Formula 1 (wt %) | Formula 2 (wt %) | Formula 3 (wt %) |
|---|---|---|---|---|
| Water | 1.2 | 1.2 | 1.2 | 15.0 |
| Corn syrup | 29.3 | 29.3 | 29.3 | 14.6 |
| Invert sugar syrup | 17.1 | 17.1 | 17.1 | 18.0 |
| Sorbitol | 3.2 | 3.2 | 3.2 | 3.2 |
| Molasses | 0.4 | 0.4 | 0.4 | 0.4 |
| Corn syrup solids | 14.5 | 14.5 | 14.5 | 14.5 |
| Soybean oil | 7.7 | 7.7 | 7.7 | 7.7 |
| Lecithin (liquid) | 0.4 | 0.4 | 0.4 | 0.4 |
| Glycerine | 10.4 | 10.4 | 10.4 | 10.4 |
| Sugar | 15.8 | — | — | — |
| Green banana powder | — | 15.8 | — | 7.9 |
| Dairy permeate | — | — | 15.8 | 7.9 |
| Total % | 100 | 100 | 100 | 100 |
| Properties | | | | |
| Water activity ($a_w$) | 0.51 | 0.54 | 0.54 | 0.66 |
| Complex Viscosity (Pascal-Sec at 25° C.) | 31.0 | 675 | 675 | 32.4 |

Given the benefit of the above disclosure and description of exemplary embodiments, it will be apparent to those skilled in the art that numerous alternate and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

The invention claimed is:

1. A modified propionibacteria for use in biosynthesis, comprising a propionibacteria having genomic DNA that includes an inserted adhE gene fragment obtained from a facultative anaerobic organism having a guanine-cytosine content of 40% or greater, such that the propionibacteria expresses a bifunctional aldehyde/alcohol dehydrogenase encoded by the nucleotide sequence set forth in SEQ ID NO:1, having activity on propionyl-CoA, wherein the modified propionibacteria produces more than double the amount of n-propanol than an unmodified Propionibacteria of the same type.

2. The modified propionibacteria of claim 1 wherein, the propionibacteria is selected from species *Propionibacterium freudenreichii* and *Propionibacterium acidipropionici*.

3. The modified propionibacteria of claim 1 or 2, wherein the facultative anaerobic organism is *Escherichia coli*.

4. A process to biosynthetically prepare n-propanol, propionic acid, or a combination thereof, comprising (a) carrying out fermentation of a starting fermentation broth comprising a substrate, water, and the modified propionibacteria of claim 1; and (b) recovering at least a portion of the product n-propanol, propionic acid, or a combination thereof from the fermentation product broth.

5. The process of claim 4 wherein the genetically modified propionibacteria is *Propionibacterium freudenreichii* or *Propionibacterium acidipropionici*.

6. The process of claim 4 or 5 wherein the facultative anaerobic organism is *Escherichia coli*.

7. The process of claim 4 or 5, wherein the starting fermentation broth further comprises stimulant n-propanol.

8. The process of claim 7 wherein the stimulant n-propanol is intracellularly produced.

9. The process of claim 8 wherein the intracellularly produced n-propanol is prepared by (a) carrying out fermentation of a broth comprising a substrate, water, and a propionibacteria that is genetically modified to include an adhE gene obtained from a facultative anaerobic organism having a guanine-cytosine content that is 40 percent or higher to express a bifunctional aldehyde/alcohol dehydrogenase encoded by the nucleotide sequence set forth in SEQ ID NO:1, with activity on propionyl-CoA, to form a fermentation product broth including intracellularly produced n-propanol; and (b) recovering at least a portion of the intracellularly produced n-propanol from the fermentation product broth.

10. The process of claim 4 or 2, wherein the substrate comprises a carbon compound selected from the group consisting of glycerol, glucose, and combination thereof.

11. The process of claim 4 or 5, wherein the starting fermentation broth exhibits catabolism of the substrate that is increased by an amount that is at least 5 percent greater than catabolism of the substrate of a starting fermentation broth that is otherwise identical but, instead of the genetically modified propionibacteria, contains an otherwise identical propionibacteria that has not been genetically modified by insertion of an adhE gene obtained from a facultative anaerobic organism having a guanine-cytosine content that is 40 percent or higher to express a bifunctional aldehyde/alcohol dehydrogenase encoded by the nucleotide sequence set forth in SEQ ID NO:1, having activity on propionyl-CoA.

12. The process of claim 4 or 5, wherein the genetically modified propionibacteria is *Propionibacterium freudenreichii* or *Propionibacterium acidipropionici*.

* * * * *

SEQUENCE LISTING

<160> NUMBER OF SEQ ID NOS: 2

<210> SEQ ID NO 1
<211> LENGTH: 2676
<212> TYPE: DNA
<213> ORGANISM: Escherichia coli str.

<400> SEQUENCE: 1

| | | | | | |
|---|---|---|---|---|---|
| ttaagcggat | ttttcgctt | tttctcagc | tttagccgga | gcagcttctt | tcttcgctgc | 60 |
| agtttcacct | tctacataat | cacgaccgta | gtaggtatcc | agcagaatct | gtttcagctc | 120 |
| ggagatcagc | gggtaacgcg | ggttagcgcc | ggtgcactgg | tcatcgaatg | catcttcaga | 180 |
| cagtttatcc | acgttcgcca | ggaagtctgc | ttcctgaacg | ccagcttcac | ggatagattt | 240 |
| cggaataccc | agttcagctt | tcagcgtttc | cagccatgcc | agcagtttct | cgatcttagc | 300 |
| agcagtacgg | tcgcccggtg | cgctcagacc | caagtggtcg | gcaatttcag | cataacgacg | 360 |
| gcgagcctgc | ggacggtcat | actggctgaa | tgcagtctgc | ttggtcgggt | tgtcgttcgc | 420 |
| attgtagcga | taacgttac | aaatcagcag | ggcgtttgcc | agaccgtgcg | gaatatggaa | 480 |
| ctgggaaccc | agtttgtgcg | ccattgagtg | acatacaccc | aggaaggcgt | tcgcaaacgc | 540 |
| gatacccgcg | atagtcgctg | cactgtgaac | acgttcacgc | gctaccggat | ttttagaccc | 600 |
| ttcgtggtag | gacgctggca | gatattcttt | cagcagtttc | agtgcctgca | gagcctgacc | 660 |
| atcagagaac | tcagatgcca | gtacagaaac | ataagcttcc | atggcgtgag | ttactgcgtc | 720 |
| cagaccaccg | aaagcacaca | gggacttcgg | catgtccata | accaggttgg | cgtcgacaat | 780 |
| cgccatatcc | ggagtcagcg | catagtctgc | cagcggatat | ttctgaccag | tagcgtcgtc | 840 |
| agttacaacc | gcaaacggag | tgacttcaga | acctgtacca | gaagtggtgg | tgacagcgat | 900 |
| cattttcgct | ttcacgccca | ttttcgggaa | cttgtagata | cgtttacgga | tatccataaa | 960 |
| gcgcagcgcg | agctcttcga | agtgagtttc | cggatgttcg | tacataaccc | acatgatctt | 1020 |
| cgcggcgtcc | atcggggaac | caccacccag | cgcgataatc | acgtctggtt | tgaaggagtt | 1080 |
| tgccagttct | gcacctttac | gaacgatgct | cagggtcggg | tccgcttcta | cttcgaagaa | 1140 |
| gacttcagtt | tcaacgcctg | ctgctttcag | tacggaagtg | atctgatcag | cataaccatt | 1200 |
| gttgaacagg | aagcggtcag | tcacgatgag | cgcacgtttg | tggccatcag | taatcacttc | 1260 |
| atccagcgcg | attggcaggg | agccacggcg | gaagtagata | gatttcggaa | gtttgtgcca | 1320 |
| caacatgttt | tcagctcgct | tagcaacggt | tttcttgttg | atcaggtgtt | tcggaccaac | 1380 |
| gttttcagag | atggagttac | caccccaaga | accacaaccc | agagtcaggg | aaggtgcgag | 1440 |
| tttgaagtta | tacaggtcac | cgataccacc | ctgagacgct | ggggtgttaa | tcaggatacg | 1500 |
| cgccgttttc | attttctgac | cgaagtaaga | aacgcgagcc | ggttggttat | cctggtcagt | 1560 |
| gtacaggcaa | gaggtatgac | cgataccgcc | catagcaacc | agtttctctg | cttttttctac | 1620 |
| cgcgtcttcg | aaatctttag | cgcggtacat | tgccagagtc | ggggacagtt | tttcatgtgc | 1680 |
| gaacggttcg | ctttcatcaa | caacggtcac | ttcaccgatc | agaatcttgg | tgttttctgg | 1740 |
| tacagagaag | cctgccagtt | cagcaatttt | ataggctggc | tgaccaacga | tagccgcgtt | 1800 |
| cagcgcaccg | ttttcagga | taacatcctg | aacagctttc | agctctttac | cctgcaacag | 1860 |
| atagccgccg | tgggttgcaa | aacgttcacg | tacagcgtca | taaacagagt | caacaacaac | 1920 |
| aacagactgt | tcagaagcac | agattacgcc | gttgtcgaag | gttttggaca | tcagtacaga | 1980 |
| tgcaactgca | cgtttgatat | cagcagtttc | atcgataaca | actggagtgt | tgcccgcgcc | 2040 |
| tacaccgata | gctggtttac | cggagctgta | tgcggcttta | accatgcccg | gaccaccagt | 2100 |

```
cgcgaggatc aggttgatgt ctgggtggtg catcagtgcg ttagacagtt caacagaagg   2160
ttgatcgatc cagccgatca gatctttcgg agcaccggca gcgatagcag cctgcagaac   2220
gatatcagcc gctttgttgg tggcatcttt tgcacgcggg tgcggggaga agataatggc   2280
gttacgggtc ttcagactga tcagcgattt gaagatagca gttgaagtcg ggttagtggt   2340
cggaacgata ccgcaaataa taccgattgg ttcagcgata gtgatggtac caaaagtgtc   2400
gtcttcagac agaacaccac aggttttttc atctttatag gcgttgtaga tatattcaga   2460
agcaaagtgg tttttgatca ctttatcttc gacgataccc atgccggatt cggcaacggc   2520
cattttcgcg agtgggattc gagcatctgc agcagccaga gcggcggcgc ggaagatttt   2580
gtctacttgc tcttgagtga aactggcata ttcacgctgg gctttttta cacgctctac   2640 gagtgcgtta agttcagcga cattagtaac agccat                             2676
```

```
<210> SEQ ID NO 2
<211> LENGTH: 891
<212> TYPE: PRT
<213> ORGANISM: Escherichia coli str.

<400> SEQUENCE: 2

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270
```

```
Leu Leu Gln Gly Lys Glu Leu Lys Ala Val Gln Asp Val Ile Leu Lys
            275                 280                 285
Asn Gly Ala Leu Asn Ala Ala Ile Val Gly Gln Pro Ala Tyr Lys Ile
        290                 295                 300
Ala Glu Leu Ala Gly Phe Ser Val Pro Glu Asn Thr Lys Ile Leu Ile
305                 310                 315                 320
Gly Glu Val Thr Val Asp Glu Ser Glu Pro Phe Ala His Glu Lys
                325                 330                 335
Leu Ser Pro Thr Leu Ala Met Tyr Arg Ala Lys Asp Phe Glu Asp Ala
                340                 345                 350
Val Glu Lys Ala Glu Lys Leu Val Ala Met Gly Gly Ile Gly His Thr
            355                 360                 365
Ser Cys Leu Tyr Thr Asp Gln Asp Asn Gln Pro Ala Arg Val Ser Tyr
        370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                405                 410                 415
Leu Thr Leu Gly Cys Gly Ser Trp Gly Gly Asn Ser Ile Ser Glu Asn
            420                 425                 430
Val Gly Pro Lys His Leu Ile Asn Lys Lys Thr Val Ala Lys Arg Ala
        435                 440                 445
Glu Asn Met Leu Trp His Lys Leu Pro Lys Ser Ile Tyr Phe Arg Arg
            450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
                485                 490                 495
Asp Gln Ile Thr Ser Val Leu Lys Ala Ala Gly Val Glu Thr Glu Val
            500                 505                 510
Phe Phe Glu Val Glu Ala Asp Pro Thr Leu Ser Ile Val Arg Lys Gly
        515                 520                 525
Ala Glu Leu Ala Asn Ser Phe Lys Pro Asp Val Ile Ile Ala Leu Gly
            530                 535                 540
Gly Gly Ser Pro Met Asp Ala Ala Lys Ile Met Trp Val Met Tyr Glu
545                 550                 555                 560
His Pro Glu Thr His Phe Glu Glu Leu Ala Leu Arg Phe Met Asp Ile
                565                 570                 575
Arg Lys Arg Ile Tyr Lys Phe Pro Lys Met Gly Val Lys Ala Lys Met
            580                 585                 590
Ile Ala Val Thr Thr Thr Ser Gly Thr Gly Ser Glu Val Thr Pro Phe
        595                 600                 605
Ala Val Val Thr Asp Asp Ala Thr Gly Gln Lys Tyr Pro Leu Ala Asp
            610                 615                 620
Tyr Ala Leu Thr Pro Asp Met Ala Ile Val Asp Ala Asn Leu Val Met
625                 630                 635                 640
Asp Met Pro Lys Ser Leu Cys Ala Phe Gly Gly Leu Asp Ala Val Thr
                645                 650                 655
His Ala Met Glu Ala Tyr Val Ser Val Leu Ala Ser Glu Phe Ser Asp
            660                 665                 670
Gly Gln Ala Leu Gln Ala Leu Lys Leu Leu Lys Glu Tyr Leu Pro Ala
            675                 680                 685
```

```
                                           -continued

Ser Tyr His Glu Gly Ser Lys Asn Pro Val Ala Arg Glu Arg Val His
    690                 695                 700
Ser Ala Ala Thr Ile Ala Gly Ile Ala Phe Ala Asn Ala Phe Leu Gly
705             710                 715                     720
Val Cys His Ser Met Ala His Lys Leu Gly Ser Gln Phe His Ile Pro
                725                 730                 735
His Gly Leu Ala Asn Ala Leu Leu Ile Cys Asn Val Ile Arg Tyr Asn
                740                 745                 750
Ala Asn Asp Asn Pro Thr Lys Gln Thr Ala Phe Ser Gln Tyr Asp Arg
            755                 760                 765
Pro Gln Ala Arg Arg Tyr Ala Glu Ile Ala Asp His Leu Gly Leu
    770                 775                 780
Ser Ala Pro Gly Asp Arg Thr Ala Ala Lys Ile Glu Lys Leu Leu Ala
785             790                 795                     800
Trp Leu Glu Thr Leu Lys Ala Glu Leu Gly Ile Pro Lys Ser Ile Arg
                805                 810                 815
Glu Ala Gly Val Gln Glu Ala Asp Phe Leu Ala Asn Val Asp Lys Leu
                820                 825                 830
Ser Glu Asp Ala Phe Asp Asp Gln Cys Thr Gly Ala Asn Pro Arg Tyr
            835                 840                 845
Pro Leu Ile Ser Glu Leu Lys Gln Ile Leu Leu Asp Thr Tyr Tyr Gly
    850                 855                 860
Arg Asp Tyr Val Glu Gly Glu Thr Ala Ala Lys Lys Glu Ala Ala Pro
865                 870                 875                 880
Ala Lys Ala Glu Lys Lys Ala Lys Lys Ser Ala
                885                 890
```